United States Patent
Zeller et al.

(10) Patent No.: US 6,864,392 B2
(45) Date of Patent: Mar. 8, 2005

(54) α-SULFIN AND α-SULFONAMINO AMIDE DERIVATIVES

(75) Inventors: Martin Zeller, Baden (CH); Clemens Lamberth, Efringen-Kirchen (DE); Henry Szczepanski, Wallbach (CH); Alain De Mesmaeker, Kaenerkinden (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 46 days.

(21) Appl. No.: 10/257,085

(22) PCT Filed: Apr. 11, 2001

(86) PCT No.: PCT/EP01/04207

§ 371 (c)(1), (2), (4) Date: Feb. 14, 2003

(87) PCT Pub. No.: WO01/79161

PCT Pub. Date: Oct. 25, 2001

(65) Prior Publication Data

US 2004/0092401 A1 May 13, 2004

(30) Foreign Application Priority Data

Apr. 13, 2000 (GB) .............................. 0009054

(51) Int. Cl.[7] ........................ C07C 311/03; A01N 41/06
(52) U.S. Cl. ...................... 564/99; 514/605; 564/138
(58) Field of Search ................... 564/99, 138; 514/605

(56) References Cited

U.S. PATENT DOCUMENTS 5,585,519 A * 12/1996 Zeller ........................... 564/79
6,194,463 B1 * 2/2001 Zeller ........................... 514/607

FOREIGN PATENT DOCUMENTS

| WO | 92/00958 | 1/1992 |
|----|----------|--------|
| WO | 95/30651 | 11/1995 |

* cited by examiner

Primary Examiner—Shailendra Kumar
(74) Attorney, Agent, or Firm—Thomas Hamilton

(57) ABSTRACT

The invention relates to novel pesticidally active α-sulfin- and α-sulfonamino acid amides of the general formula (I) including the optical isomers thereof and mixtures of such isomers, wherein n is a number zero or one, $R_1$–$R_7$ have the meanings given in the specification. $R_8$ is either hydrogen, (a), (b), (c), (d) or (e) wherein $R_{11}$, $R_{12}$, $R_{14}$, $R_{15}$ and $R_{17}$ are each independently hydrogen or $C_1$–$C_4$alkyl, $R_{13}$ is $C_4$–$C_{12}$alkyl; $C_1$–$C_{12}$ halogenalkyl; $C_3$–$C_8$ cycloalkyl; optionally substituted aryl or optionally substituted heteroaryl, $R_{16}$ is optionally substituted aryl or optionally substituted heteroaryl; and Z is oxygen, sulfur —$CR_{18}R_{19}$— or —$NR_{20}$—, wherein $R_{18}$, $R_{19}$, $R_{20}$ independently of each other are hydrogen or $C_1$–$C_4$alkyl. The novel compounds possess plant-protecting properties and are suitable for protecting plants against infestation by phytopathogenic microorganisms (I)

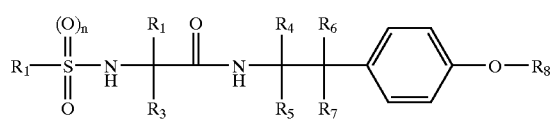

(a)

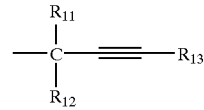

(b)

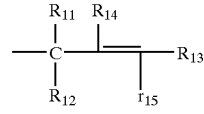

(c)

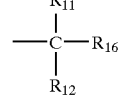

(d)

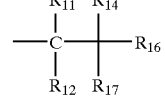

(e)

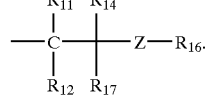

15 Claims, No Drawings

α-SULFIN AND α-SULFONAMINO AMIDE DERIVATIVES

This application is a 371 of PCT/EP01/04207, filed Apr. 11, 2001.

The present invention relates to novel α-sulfin and α-sulfonamino acid amides of formula I below. It relates to the preparation of those substances and to agrochemical compositions comprising at least one of those compounds as active ingredient. The invention relates also to the preparation of the said compositions and to the use of the compounds or of the compositions in controlling or preventing the infestation of plants by phytopathogenic microorganisms, especially fungi.

The invention relates to α-sulfin- and α-sulfonamino acid amides of the general formula I

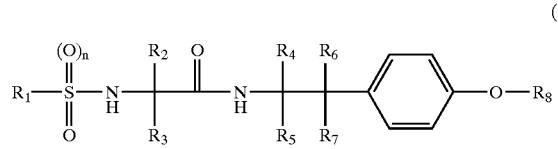

(I)

including the optical isomers thereof and mixtures of such isomers, wherein n is a number zero or one;

$R_1$ is $C_1$–$C_{12}$alkyl, $C_1$–$C_{12}$alkyl substituted with $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_8$alkenyloxycarbonyl or $C_3$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$halogenalkyl; or a group $NR_9R_{10}$ wherein $R_9$ and $R_{10}$ are each independently of the other hydrogen or $C_1$–$C_6$alkyl, or together are tetra- or penta-methylene;

$R_2$ and $R_3$ are each independently hydrogen; $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl; or the two groups $R_2$ and $R_3$ together with the carbon atom to which they are bonded form a three- to eight-membered hydrocarbon ring;

$R_4$, $R_5$, $R_6$ and $R_7$ are each independently hydrogen or $C_1$–$C_4$alkyl;

$R_8$ is either hydrogen,

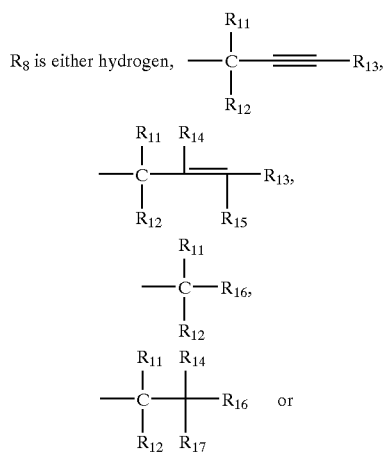

-continued

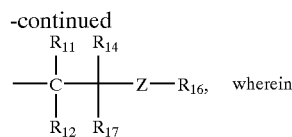

wherein $R_{11}$, $R_{12}$, $R_{14}$, $R_{15}$ and $R_{17}$ are each independently hydrogen or $C_1$–$C_4$alkyl, $R_{13}$ is $C_4$–$C_{12}$alkyl; $C_1$–$C_{12}$halogenalkyl; $C_3$–$C_8$cycloalkyl; optionally substituted aryl or optionally substituted heteroaryl, $R_{16}$ is optionally substituted aryl or optionally substituted heteroaryl, and Z is oxygen, sulfur —$CR_{18}R_{19}$— or —$NR_{20}$—, wherein $R_{18}$, $R_{19}$ and $R_{20}$ independently of each other are hydrogen or $C_1$–$C_4$alkyl.

In the above definition aryl includes aromatic hydrocarbon rings like phenyl, naphthyl, anthracenyl, phenanthrenyl, with phenyl being preferred.

Heteroaryl stands for aromatic ring systems comprising mono-, bi- or tricyclic systems wherein at least one oxygen, nitrogen or sulfur atom is present as a ring member. Examples are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The above aryl and heteroaryl groups may carry one or more identical or different substituents. Normally not more than three substituents are present at the same time. Examples of substituents of aryl or heteroaryl groups are: alkyl, alkenyl, alkynyl, cycloalkyl, cycloalkyl-alkyl, phenyl and phenyl-alkyl, it being possible in turn for all of the preceding groups to carry one or more identical or different halogen atoms; alkoxy; alkenyloxy; alkynyloxy; alkoxy-alkyl; halogenalkoxy, alkylthio; halogenalkylthio; alkyl sulfonyl; formyl; alkanoyl; hydroxy; halogen; cyano; nitro; amino; alkylamino; dialkyl amino; carboxy; alkoxycarbonyl; alkenyloxycarbonyl; alkynyloxycarbonyl.

In the above definitions "halogen" or the prefix "halo" includes fluorine, chlorine, bromine and iodine.

The alkyl, alkenyl and alkynyl radicals may be straight-chain or branched. This applies also to the alkyl, alkenyl or alkynyl parts of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl, hexyl, heptyl, octyl, nonyl, decyl, undecyl, dodecyl and the isomers thereof, for example isopropyl, isobutyl, tert-butyl or sec-butyl, isopentyl or tert-pentyl.

Cycloalkyl is, depending upon the number of carbon atoms mentioned, cyclopropyl, cyclobutyl, cyclopentyl, cyclohexyl, cycloheptyl or cyclooctyl.

Depending upon the number of carbon atoms mentioned, alkenyl as a group or as a structural element of other groups is to be understood as being, for example, ethenyl, allyl, 1-propenyl, buten-2-yl, buten-3-yl, penten-1-yl, penten-3-yl, hexen-1-yl, 4-methyl-3-pentenyl or 4-methyl-3-hexenyl.

Alkynyl as a group or as a structural element of other groups is, for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl.

A halogenalkyl group may contain one or more (identical or different) halogen atoms, and for example may stand for $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, etc.

Where $R_2$ and $R_3$ together with the carbon atom to which they are attached form a hydrocarbon ring the ring corresponds to cyclopropane, cyclobutane, cyclopentane, cyclohexane, cycloheptane or cyclooctane.

Where $R_9$ and $R_{10}$ together with the nitrogen atom to which they are attached form a ring system the ring corresponds to pyrrolidine or piperidine.

The presence of at least one asymmetric carbon atom and/or at least one asymmetric oxidized sulfur atom in the compounds of formula I means that the compounds may occur in optically isomeric forms. As a result of the presence of a possible aliphatic C=C double bond, geometric isomerism may also occur. Formula I is intended to include all those possible isomeric forms and mixtures thereof.

Preferred subgroups of compounds of formula I are those wherein n is one; or $R_1$ is $C_1$–$C_{12}$alkyl, $C_1$–$C_{12}$alkyl substituted with $C_1$–$C_4$alkoxy, $C_1$–$C_4$alkylthio, or $C_1$–$C_4$alkylsulfonyl; $C_3$–$C_8$cycloalkyl; $C_2$–$C_{12}$alkenyl; $C_2$–$C_{12}$alkynyl; $C_1$–$C_{12}$halogenalkyl; or a group $NR_9R_{10}$ wherein $R_9$ and $R_{10}$ are each independently of the other hydrogen or $C_1$–$C_6$alkyl, or together are tetra- or pentamethylene; or $R_1$ is $C_1$–$C_{12}$alkyl, $C_2$–$C_{12}$alkenyl; $C_1$–$C_{12}$halogenalkyl; or a group $NR_9R_{10}$ wherein $R_9$ and $R_{10}$ are each independently of the other hydrogen or $C_1$–$C_6$alkyl; or $R_1$ is $C_1$–$C_4$alkyl, $C_2$–$C_4$alkenyl; $C_1$–$C_4$halogenalkyl; or $C_1$–$C_2$dialkylamino; or $R_1$ is $C_1$–$C_4$alkyl, vinyl; $C_1$–$C_4$halogenalkyl; or dimethylamino; or $R_2$ is hydrogen and $R_3$ is $C_1$–$C_8$alkyl, $C_1$–$C_8$alkyl optionally substituted by hydroxy, $C_1$–$C_4$-alkoxy, mercapto or $C_1$–$C_4$alkylthio; $C_3$–$C_8$alkenyl; $C_3$–$C_8$alkynyl; $C_3$–$C_8$cycloalkyl or $C_3$–$C_8$cycloalkyl-$C_1$–$C_4$alkyl; or $R_2$ is hydrogen and $R_3$ is $C_1$–$C_4$alkyl; $C_3$–$C_4$alkenyl or cyclopropyl; or $R_2$ is hydrogen and $R_3$ is $C_3$–$C_4$alkyl; allyl or cyclopropyl; or $R_2$ is hydrogen and $R_3$ is isopropyl; or $R_4$ is hydrogen, methyl or ethyl; or $R_4$ is hydrogen or methyl; or $R_4$ is hydrogen; or $R_5$, $R_6$ and $R_7$ are each independently hydrogen or methyl; or $R_5$, $R_6$ and $R_7$ are each hydrogen; or $R_{11}$, $R_{12}$, $R_{14}$, $R_{15}$ and $R_{17}$ are each independently hydrogen or methyl; or $R_{11}$, $R_{12}$, $R_{14}$, $R_{15}$ and $R_{17}$ are each hydrogen; or $R_{13}$ is $C_4$–$C_{12}$alkyl; $C_1$–$C_{12}$halogenalkyl; $C_3$–$C_8$cycloalkyl; optionally substituted aryl or optionally substituted heteroaryl consisting of one or two condensed five or six membered rings with 1 to 4 identical or different heteroatoms selected from oxygen, nitrogen or sulfur; or $R_{13}$ is $C_4$–$C_{12}$alkyl; $C_1$–$C_{12}$halogenalkyl; $C_3$–$C_8$cycloalkyl; phenyl, naphthyl, furyl, thienyl, pyrrolyl, imidazolyl, pyrazolyl, thiazolyl, oxazolyl, isoxazolyl, thiazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl with each of the aromatic ring being optionally substituted by 1 to 3 substituents selected from the group consisting of $C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl wherein the hydrogens of all these substituents may be optionally substituted by one or more identical or different halogen atoms; $C_1$–$C_8$alkoxy, $C_3$–$C_8$alkenyloxy, $C_3$–$C_8$alkynyloxy, $C_1$–$C_8$alkoxy-$C_1$–$C_4$alkyl, $C_1$–$C_8$halogenalkoxy, $C_1$–$C_8$alkylthio, $C_1$–$C_8$halogenalkylthio, $C_1$–$C_8$alkylsulfonyl, formyl, $C_2$–$C_8$alkanoyl, hydroxy, halogen, cyano, nitro, amino and $C_1$–$C_8$alkylamino, $C_1$–$C_8$dialkylamino, carboxy, $C_1$–$C_8$alkoxycarbonyl, $C_1$–$C_8$alkenyloxycarbonyl and $C_1$-$C_8$alkynyloxycarbonyl; or $R_{13}$ is $C_4$–$C_{12}$alkyl; $C_1$–$C_1$-halogenalkyl; $C_3$–$C_8$cycloalkyl; phenyl, naphthyl, thienyl, pyridyl, pyrimidinyl, triazinyl, or quinolyl with each of the aromatic ring being optionally substituted by 1 to 3 substituents selected from the group consisting of $C_1$–$C_8$-alkyl, $C_2$–$C_8$alkenyl, wherein the hydrogens of all these substituents may be optionally substituted by one or more identical or different halogen atoms; $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl; or $R_{13}$ is $C_4$–$C_8$alkyl; $C_1$–$C_6$halogenalkyl; $C_3$–$C_8$cycloalkyl; phenyl, pyridyl, with each of the aromatic ring being optionally substituted by 1 to 3 substituents selected from the group consisting of $C_1$–$C_8$alkyl, $C_1$–$C_8$halogenalkyl, $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl; or $R_{16}$ is optionally substituted aryl or optionally substituted heteroaryl consisting of one or two condensed five or six membered rings with 1 to 4 identical or different heteroatoms selected from oxygen, nitrogen or sulfur; or $R_{16}$ is phenyl, naphthyl, furyl, thienyl, pyrrolyl, imidazolyl, pyrazolyl, thiazolyl, oxazolyl, isoxazolyl, thiazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl with each of the aromatic ring being optionally substituted by 1 to 3 substituents selected from the group consisting of $C_1$–$C_8$alkyl, $C_2$–$C_8$alkenyl, $C_2$–$C_8$alkynyl, $C_3$–$C_8$-cycloalkyl, $C_3$–$C_8$cycloalkyl-$C_1$–$C_4$alkyl, phenyl, phenyl-$C_1$–$C_4$alkyl wherein the hydrogens of all these substituents may be optionally substituted by one or more identical or different halogen atoms; $C_1$–$C_8$alkoxy, $C_3$–$C_8$alkenyloxy, $C_3$–$C_8$alkynyloxy, $C_1$–$C_8$alkoxy-$C_1$–$C_4$alkyl, $C_1$–$C_8$halogenalkoxy, $C_1$–$C_8$alkylthio, $C_1$–$C_8$halogenalkylthio, $C_1$–$C_8$alkylsulfonyl, formyl, $C_2$–$C_8$alkanoyl, hydroxy, halogen, cyano, nitro, amino, $C_1$–$C_8$alkylamino, $C_1$–$C_8$dialkylamino, carboxy, $C_1$–$C_8$alkoxycarbonyl, $C_1$–$C_8$alkenyloxycarbonyl and $C_1$–$C_8$alkynyloxycarbonyl; or $R_{16}$ is phenyl, naphthyl, thienyl, pyridyl, pyrimidinyl, triazinyl, or quinolyl with each of the aromatic ring being optionally substituted by 1 to 3 substituents selected from the group consisting of $C_1$–$C_8$alkyl, $C_2$–$C_8$alkenyl, wherein the hydrogens of all these substituents may be optionally substituted by one or more identical or different halogen atoms; $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl; or $R_{16}$ is phenyl, pyridyl, with each of the aromatic ring being optionally substituted by 1 to 3 substituents selected from the group consisting of $C_1$–$C_8$alkyl, $C_1$–$C_8$halogenalkyl, $C_1$–$C_8$alkoxy, $C_1$–$C_8$halogenalkoxy, $C_1$–$C_8$alkylthio, $C_1$–$C_8$-halogenalkylthio, halogen, cyano, nitro and $C_1$–$C_8$alkoxycarbonyl; or Z is oxygen, sulfur or —$CH_2$—; or Z is oxygen.

Further preferred subgroups of the compounds of formula I are those wherein

1) $R_1$ is $C_1$–$C_{12}$alkyl, $C_1$–$C_{12}$alkyl substituted with $C_1$–$C_4$alkoxy, $C_1$–$C_4$alkylthio, or $C_1$–$C_4$alkylsulfonyl; $C_3$–$C_8$cycloalkyl; $C_2$–$C_{12}$alkenyl; $C_2$–$C_{12}$alkynyl; $C_1$–$C_{12}$halogenalkyl; or a group $NR_9R_{10}$ wherein $R_9$ and $R_{10}$ are each independently of the other hydrogen or $C_1$–$C_6$alkyl, or together are tetra- or penta-methylene;

$R_2$ is hydrogen and $R_3$ is $C_1$–$C_8$alkyl; $C_1$–$C_8$alkyl substituted with hydroxy, mercapto, $C_1$–$C_4$alkoxy or $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl;

$R_{13}$ is $C_4$–$C_{12}$-alkyl; $C_1$–$C_{12}$-halogenalkyl; $C_3$–$C_8$cycloalkyl; optionally substituted aryl or optionally substituted heteroaryl consisting of one or two condensed five or six membered rings with 1 to 4 identical or different heteroatoms selected from oxygen, nitrogen or sulfur; and $R_{16}$ is optionally substituted aryl or optionally substituted heteroaryl consisting of one or two condensed five or six membered rings with 1 to 4 identical or different heteroatoms selected from oxygen, nitrogen or sulfur; or 2) n is one;

$R_1$ is $C_1$–$C_{12}$alkyl, $C_2$–$C_{12}$alkenyl; $C_1$–$C_{12}$halogenalkyl; or a group $NR_9R_{10}$ wherein $R_9$ and $R_{10}$ are each independently of the other hydrogen or $C_1$–$C_6$alkyl;

$R_2$ is hydrogen and $R_3$ is $C_1$–$C_4$alkyl; $C_3$–$C_4$alkenyl or cyclopropyl;

$R_4$ is hydrogen, methyl or ethyl; or $R_5$, $R_6$, $R_7$, $R_{11}$, $R_{12}$, $R_{14}$, $R_{15}$ and $R_{17}$ are each independently hydrogen or methyl;

$R_{13}$ is $C_4$–$C_{12}$alkyl; $C_1$–$C_{12}$-halogenalkyl; $C_3$–$C_8$-cycloalkyl; phenyl, naphthyl, furyl, thienyl, pyrrolyl, imidazolyl, pyrazolyl, thiazolyl, oxazolyl, isoxazolyl, thiazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl with each of the aromatic ring being optionally substituted by 1 to 3 substituents selected from the group consisting of $C_1$–$C_8$alkyl, $C_2$–$C_8$alkenyl, $C_2$–$C_8$alkynyl, $C_3$–$C_8$cycloalkyl, $C_3$–$C_8$cycloalkyl -$C_1$–$C_4$alkyl, phenyl, phenyl-$C_1$–$C_4$alkyl wherein the hydrogens of all these substituents may be optionally substituted by one or more identical or different halogen atoms; $C_1$–$C_8$alkoxy, $C_3$–$C_8$alkenyloxy, $C_3$–$C_8$alkynyloxy, $C_1$–$C_8$alkoxy-$C_1$–$C_4$alkyl, $C_1$–$C_8$halogenalkoxy, $C_1$–$C_8$alkylthio, $C_1$–$C_8$halogenalkylthio, $C_1$–$C_8$alkylsulfonyl, formyl, $C_2$–$C_8$alkanoyl, hydroxy, halogen, cyano, nitro, amino and $C_1$–$C_8$-dialkylamino, carboxy, $C_1$–$C_8$-alkoxycarbonyl, $C_1$–$C_8$-alkenyloxycarbonyl and $C_1$–$C_8$alkynyloxycarbonyl;

$R_{16}$ is phenyl, naphthyl, furyl, thienyl, pyrrolyl, imidazolyl, pyrazolyl, thiazolyl, oxazolyl, isoxazolyl, thiazolyl, pyridyl, pyridazinyl, pyrimidinyl, pyrazinyl, triazinyl, indolyl, benzothiophenyl, benzofuranyl, benzimidazolyl, benzthiazolyl, benzoxazolyl or quinolyl with each of the aromatic ring being optionally substituted by 1 to 3 substituents selected from the group consisting of $C_1$–$C_8$-alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl wherein the hydrogens of all these substituents may be optionally substituted by one or more identical or different halogen atoms; $C_1$–$C_8$alkoxy, $C_3$–$C_8$alkenyloxy, $C_3$–$C_8$alkynyloxy, $C_1$–$C_8$alkoxy-$C_1$–$C_4$alkyl, $C_1$–$C_8$halogenalkoxy, $C_1$–$C_8$alkylthio, $C_1$–$C_8$halogenalkylthio, $C_1$–$C_8$alkylsulfonyl, formyl, $C_2$–$C_8$alkanoyl, hydroxy, halogen, cyano, nitro, amino and $C_1$–$C_8$alkylamino, $C_1$–$C_8$dialkylamino, carboxy, $C_1$–$C_8$alkoxycarbonyl, $C_1$–$C_8$alkenyloxycarbonyl and $C_1$–$C_8$alkynyloxycarbonyl; and Z is oxygen, sulfur or —$CH_2$—; or 3) n is one;

$R_1$ is $C_1$–$C_4$alkyl, $C_2$–$C_4$alkenyl; $C_1$–$C_4$halogenalkyl; or $C_1$–$C_2$-dialkylamino;

$R_2$ is hydrogen and $R_3$ is $C_3$–$C_4$alkyl; allyl or cyclopropyl;

$R_4$ is hydrogen or methyl;

$R_5$, $R_6$, $R_7$, $R_{11}$, $R_{12}$, $R_{14}$, $R_{15}$ and $R_{17}$ are each hydrogen;

$R_{13}$ is $C_4$–$C_{12}$alkyl; $C_1$–$C_{12}$halogenalkyl; $C_3$–$C_8$cycloalkyl; phenyl, naphthyl, thienyl, pyridyl, pyrimidinyl, triazinyl, or quinolyl with each of the aromatic ring being optionally substituted by 1 to 3 substituents selected from the group consisting of $C_1$–$C_8$alkyl, $C_2$–$C_8$alkenyl, wherein the hydrogens of all these substituents may be optionally substituted by one or more identical or different halogen atoms; $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl;

$R_{16}$ is phenyl, naphthyl, thienyl, pyridyl, pyrimidinyl, triazinyl, or quinolyl with each of the aromatic ring being optionally substituted by 1 to 3 substituents selected from the group consisting of $C_1$–$C_8$alkyl, $C_2$–$C_8$alkenyl, wherein the hydrogens of all these substituents may be optionally substituted by one or more identical or different halogen atoms; $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl; and Z is oxygen, sulfur or —$CH_2$—; or 4) n is one;

$R_1$ is $C_1$–$C_4$alkyl, vinyl; $C_1$–$C_4$halogenalkyl; or dimethylamino;

$R_2$ is hydrogen and $R_3$ is isopropyl;

$R_4$, $R_5$, $R_6$, $R_7$, $R_{11}$, $R_{12}$, $R_{14}$, $R_{15}$ and $R_{17}$ are each hydrogen;

$R_{13}$ is $C_4$–$C_8$alkyl; $C_1$–$C_6$halogenalkyl; $C_3$–$C_8$cycloalkyl; phenyl, pyridyl, with each of the aromatic ring being optionally substituted by 1 to 3 substituents selected from the group consisting of $C_1$–$C_8$alkyl, $C_1$–$C_8$halogenalkyl, $C_1$–$C_8$alkoxy, $C_1$–$C_8$halogenalkoxy, $C_1$–$C_8$alkylthio, $C_1$–$C_8$-halogenalkylthio, halogen, cyano, nitro and $C_1$–$C_8$alkoxycarbonyl;

$R_{16}$ is phenyl, pyridyl, with each of the aromatic ring being optionally substituted by 1 to 3 substituents selected from the group consisting of $C_1$–$C_8$alkyl, $C_1$–$C_8$halogenalkyl, $C_1$–$C_8$alkoxy, $C_1$–$C_8$halogenalkoxy, $C_1$–$C_8$alkylthio, $C_1$–$C_8$halogenalkylthio, halogen, cyano, nitro and $C_1$–$C_8$alkoxycarbonyl; and Z is oxygen.

Preferred individual compounds are:

N-(2-{4-[3-(4-chloro-phenyl))-prop-2-ynyloxy]-phenyl}-ethyl)-2-methanesulfonyalmino-3-methyl-butyramide, N-(2-{4-[3-(4-fluoro-phenyl)-prop-2-ynyloxy]-phenyl}-ethyl)-2-methanesulfonylamino-3-methyl-butyramide, N-(2-{4-[3-(4-bromo-phenyl)-prop-2-ynyloxy]-phenyl}-ethyl)-2-methanesulfonylamino-3-methyl-butyramide, N-(2-{4-[3-(p-tolyl)-prop-2-ynyloxy]-phenyl}-ethyl)-2-methanesulfonylamino-3-methyl-butyramide, N-{2-[4-(3-cyclopropyl-prop-2-ynyloxy)-phenyl]-ethyl}-2-methanesulfonylamino-3-methyl-butyramide, N-(2-{4-[3-(4-chloro-phenyl)-prop-2-ynyloxy]-phenyl}-ethyl)-2-ethanesulfonylamino-3-methyl-butyramide, N-(2-{4-[3-(4-fluoro-phenyl)-prop-2-ynyloxy]-phenyl}-ethyl)-2-ethanesulfonylamino-3-methyl-butyramide, N-(2-{4-[3-(4-bromo-phenyl)-prop-2-ynyloxy]-phenyl}-ethyl)-2-ethanesulfonylamino-3-methyl-butyramide, N-(2-{4-[3-(p-tolyl)-prop-2-ynyloxy]-phenyl}-ethyl)-2-ethanesulfonylamino-3-methyl-butyramide, and N-{2-[4-(3-cyclopropyl-prop-2-ynyloxy)-phenyl]-ethyl}-2-ethanesulfonylamino-3-methyl-butyramide.

Certain α-sulfin- and α-sulfonamino acid derivatives having a different kind of molecular structure have already been proposed for controlling plant-destructive fungi (for example in WO 95/030651, WO 97/14677, WO 98/38160, WO 98/38161 and WO 99/07674).

However, the activity of the known compounds is not always satisfactory in all aspects of agricultural needs. Surprisingly, with the compound structure of formula I, a new kind of microbiocides have been found showing an improved systemic activity in plants against phytopathogenic microorganisms, especially fungi.

The α-sulfin- and α-sulfonamino acid amides of formula I may be obtained according to one of the following processes:

a)

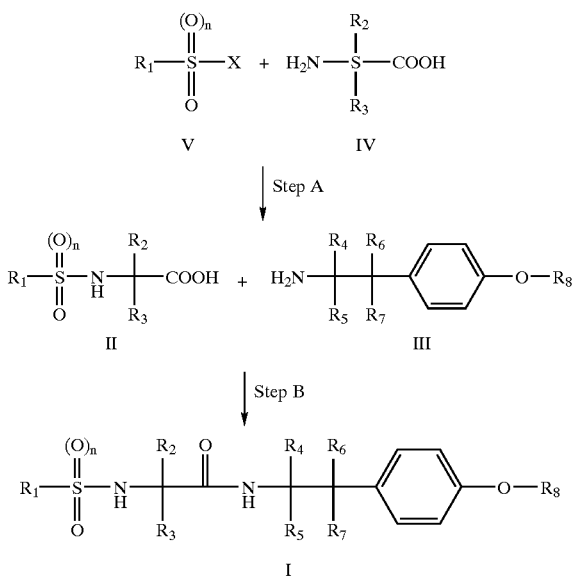

An amino acid of formula II or a carboxy-activated derivative of an amino acid of formula II wherein $R_1$, n, $R_2$ and $R_3$ are as defined for formula I is reacted with an amine of formula III wherein $R_4$, $R_5$, $R_6$, $R_7$ and $R_8$ are as defined above optionally in the presence of a base and optionally in the presence of a diluting agent (step B).

Carboxy-activated derivatives of the amino acid of formula II encompasses all compounds having an activated carboxyl group like an acid halide, such as an acid chloride, like symmetrical or mixed anhydrides, such as mixed anhydrides with O-alkylcarbonates, like activated esters, such as p-nitrophenylesters or N-hydroxysuccinimidesters, as well as in situ produced activated forms of the amino acid of formula II by condensating agents, such as dicyclohexylcarbodiimide, carbonyldiimidazol, benzotriazol-1-yloxy-tris (dimethylamino)phosphonium hexafluorophosphate, O-benzotriazol-1-yl N,N,N',N'-bis (penta methylene)uronium hexafluorophosphate, O-benzotriazol-1-yl N,N,N',N'-bis(tetramethylene)uronium hexafluorophosphate, O-benzotriazol-1-yl N,N,N',N'-tetramethyluronium hexafluoro-phosphate or benzotriazol-1-yloxy-tripyrrolidino phosphonium hexafluorophosphate. The mixed anhydrides of the amino acids of the formula II may be prepared by reaction of an amino acid of formula II with chloroformic acid esters like chloroformic acid alkylesters, such as ethyl chloroformate or isobutyl chloroformate, optionally in the presence of an organic or inorganic base like a tertiary amine, such as triethylamine, N,N-diisopropyl-ethylamine, pyridine, N-methyl-piperidine or N-methyl-morpholine.

The present reaction is preferably performed in an inert solvent like aromatic, non-aromatic or halogenated hydrocarbons, such as chlorohydrocarbons e.g. dichloromethane or toluene; ketones, e.g. acetone; esters, e.g. ethyl acetate; amides, e.g. N,N-dimethylformamide; nitriles e.g. acetonitrile; or ethers e.g. diethylether, tert-butyl-methylether, dioxane or tetrahydrofurane or water. It is also possible to use mixtures of these solvents. The reaction is preformed optionally in the presence of an organic or inorganic base like a tertiary amine, e.g. triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from –80° C. to +150° C., preferentially at temperatures ranging from –40° C. to +40° C.

The compounds of formula II may be prepared by reaction of an amino acid of formula IV where $R_2$ and $R_3$ are as defined for formula I with a sulfonyl halide or a sulfinyl halide of formula V where $R_1$ and n have the same meanings as defined above and where X is halide, preferentially chlorine or bromine (step A).

The reaction may be performed in an inert solvent like aromatic, non-aromatic or halogenated hydrocarbons, such as chlorohydrocarbons, e.g. dichloromethane or toluene; ketones, e.g. acetone; esters, e.g. ethyl acetate; ethers, e.g. diethylether, tert-butyl-methylether, dioxane or tetrahydrofurane or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide or a metal carbonate, preferentially an alkali hydroxide or an alkali carbonate, such as lithium hydroxide, sodium hydroxide or potassium hydroxide at temperatures ranging from –80° C. to +150° C., preferentially at temperatures ranging from –40° C. to +40° C.

b)

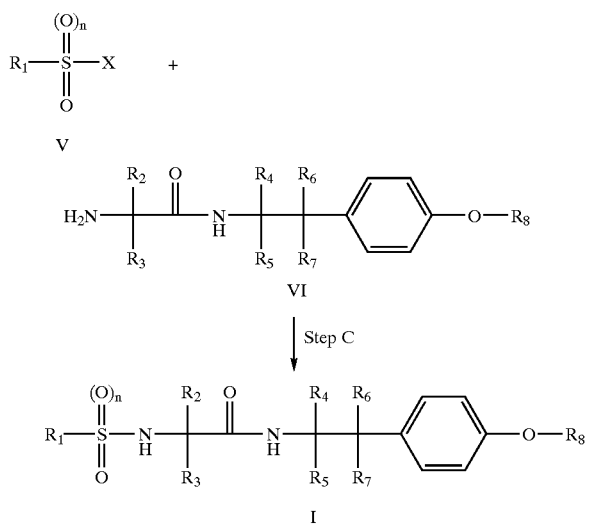

The compounds of formula I may also be prepared by reaction of an amino acid derivative of formula VI wherein $R_2$, $R_3$, $R_4$, $R_5$, $R_6$, $R_7$ and $R_8$ are as defined for formula I with a sulfonyl halide or a sulfinyl halide of formula V wherein $R_1$ and n are as defined for formula I and X is halide, preferentially chlorine or bromine (step C). The reaction is performed in the same manner as described for step A.

c)

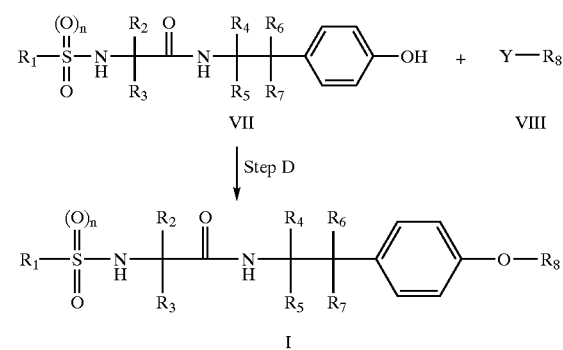

The compounds of formula I may also be prepared by reaction of a phenol of formula VII wherein $R_1$, n, $R_2$, $R_3$, $R_4$, $R_5$, $R_6$ and $R_7$ are as defined for formula I with a compound of formula VIII wherein $R_8$ is as defined for formula I and Y is a leaving group like a halide such as a chloride or bromide or a sulfonic ester such as a tosylate, mesylate or triflate (step D). The reaction may be performed in an inert solvent like aromatic, non-aromatic or halogenated hydrocarbons, such as chlorohydrocarbons e.g. dichloromethane or toluene; ketones e.g. acetone or 2-butanone; esters, e.g. ethyl acetate; ethers, e.g. diethylether, tert-butylmethylether, dioxane or tetrahydrofurane, amides, e.g. dimethylformamide, nitriles, e.g. acetonitrile, alcohols, e.g. methanol, ethanol, isopropanol, n-butanol or tert-butanol, sulfoxides e.g. dimethylsulfoxide or water. It is also possible to use mixtures of these solvents. The reaction is performed optionally in the presence of an organic or inorganic base like a tertiary amine, such as triethylamine, N,N-diisopropyl-ethylamine, pyridine, N-methyl-piperidine or N-methyl-morpholine, like a metal hydroxide, a metal carbonate or a metal alkoxide, preferentially an alkali hydroxide, an alkali carbonate or an alkali alkoxide, such as lithium hydroxide, sodium hydroxide, potassium hydroxide, sodium carbonate, potassium carbonate, sodium methoxide, potassium methoxide, sodium ethoxide, potassium ethoxide, sodium tert-butoxide or potassium tert-butoxide at temperatures ranging from −80° C. to +200° C., preferentially at temperatures ranging from 0° C. to +120° C.

d)

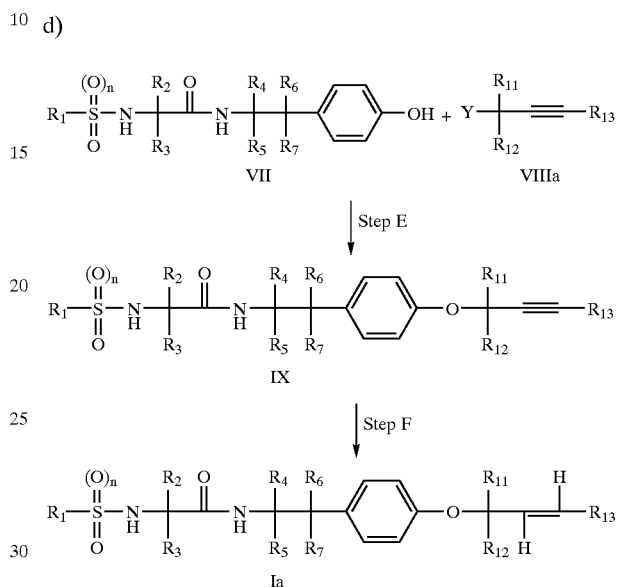

The compounds of formula Ia may also be prepared via formula IX wherein $R_1$, n, $R_2$, $R_3$, $R_4$, $R_5$, $R_6$, $R_7$, $R_{11}$, $R_{12}$ and $R_{13}$ are defined for formula I by reacting of a phenol of formula VII wherein $R_1$, n, $R_2$, $R_3$, $R_4$, $R_5$, $R_6$ and $R_7$ are as defined for formula I with a compound of formula VIIIa wherein $R_{11}$, $R_{12}$ and $R_{13}$ are as defined for formula I and Y is a leaving group like a halide such as a chloride or bromide or a sulfonic ester such as a tosylate, mesylate or triflate (step E).

The reaction is performed in the same manner as described for step D.

The compounds of formula Ia $R_{11}$, $R_{12}$ and $R_{13}$ is as defined for formula I may be prepared by reaction of compounds of formula IX with hydrogen.

The reaction is performed in a solvent like ethers, e.g. diethylether, dioxane or tetrahydrofuran, or like alcohols, e.g. methanol or ethanol, or water in the presence of transition metals or transition metal salts, e.g. nickel, cobalt, palladium, platinum or rhodium, optionally in the presence of bases, e.g. ammonia, or in the presence of salts, e.g. barium sulfate, at temperatures ranging from −20° C. to +160° C. and at pressures ranging from 1 to 200 bar.

aa) The intermediate amines of formula III may be obtained by one of the following processes:

Procedure 1:

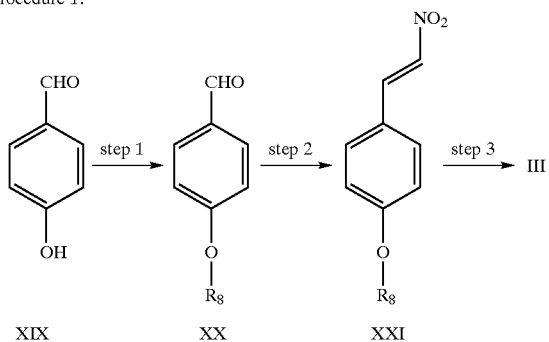

Procedure 2:

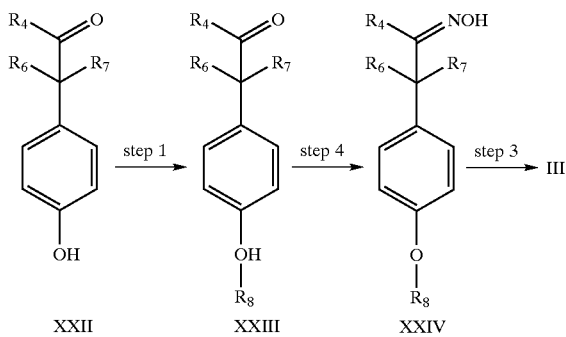

Procedure 3:

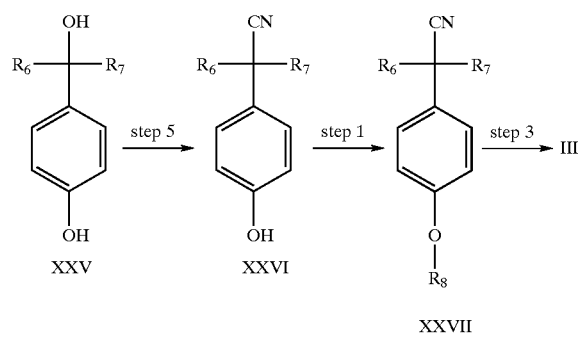

Procedure 4:

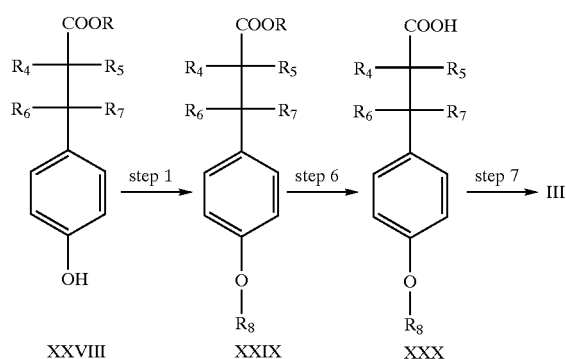

Step 1 is the alkylation of a phenol with a compound of formula VIII. The reaction is performed in the same manner as described for procedure c).

Step 2 is the reaction of an aromatic aldehyde with nitromethane. This reaction is performed in a solvent like an organic carboxylic acids, e.g. acetic acid optionally in the presence of the ammonium salt of this carboxylic acid, e.g. ammonium acetate at temperatures ranging from 0° C. to +200° C.

Step 3 is the reduction of an unsaturated nitrogen-compound. This reaction is performed in a solvent like an ether, e.g. diethylether, dioxane or tetrahydrofuran, or an alcohol, e.g. methanol, ethanol or isopropanol, with borohydride, with a boron-complex, e.g. the complex of borohydride with tetrahyrofuran, with an alkaliborohydride, with an alkalialuminiumhydride, e.g. lithiumaluminiumhydride, with aluminiumhydride, with an aluminiumalkoxyhydride or with hydrogen optionally in the presence of a transition metal, a transition metal salt or a transition metal complex, e.g. nickel, cobalt, palladium, platinium or rhodium at temperatures ranging from −50° C. to +200° C.

Step 4 is the reaction of an aldehyde or a ketone of formula XXIII with hydroxylamine or with a salt of hydroxylamine. This reaction is performed in a solvent like an alcohol, e.g. methanol, ethanol or isopropanol, like an ether, e.g. diethylether, dioxane or tetrahydrofuran, like an amide, e.g. dimethylformamide, or in water or in a mixture of these solvents optionally in the presence of an organic or inorganic base like a tertiary amine, e.g. triethylamine, like a heterocyclic compound containing nitrogen, e.g. pyridine, or like an alkalicarbonate, e.g. sodium carbonate or potassium carbonate, at temperatures ranging from −20° C. to +150° C.

Step 5 is the exchange of hydroxy by cyanide. This reaction is performed in an organic solvent like an amide, e.g. dimethylformamide using a metal cyanide like an alkali cyanide, e.g. sodium cyanide or potassium cyanide, at temperatures ranging from 0° C. to +200° C.

Step 6 is the hydrolysis of an alkyl ester. This reaction is performed in a solvent like an alcohol, e.g. methanol, ethanol or isopropanol, like an ether, e.g. diethylether, dioxane or tetrahydrofuran, like a halogenated hydrocarbon, e.g. dichloromethane, or water or in a mixture of these solvents optionally in the presence of an alkali hydroxide, e.g. lithium hydroxide, sodium hydroxide or potassium hydroxide, or optionally in the presence of an acid, e.g. hydrogen chloride, sulfuric acid or trifluoroacetic acid at temperatures ranging from −20° C. to +160° C.

Step 7 is the reaction of a carboxylic acid or the activated form of this carboxylic acid with hydrogen azide or an azide-salt. An activated form of a carboxylic acid can be the acid halogenide, e.g. acid chloride, a symmetric or a mixed anhydride. Azide-salts can be alkali azides, e.g. sodium azide. The reaction is performed in a solvent like a hydrocarbon, e.g. toluene or xylene, like a halogenated hydrocarbon, e.g. chloroform, like an ether, e.g. dioxane, like a ketone, e.g. acetone or 2-butanone, like an alcohol, e.g. methanol, ethanol or tert-butanol, or water or in a mixture of these solvents optionally in the presence of an acid like an inorganic acid, e.g. sulfuric acid or hydrogen chloride at temperatures ranging from −40° C. to +200° C.

In a preferred form the compounds of formula XXVI are prepared starting from compounds of the formula XXV by applying step 5 and step 1 in the same pot.

bb) Amines of formula VI can be obtained by the following process:

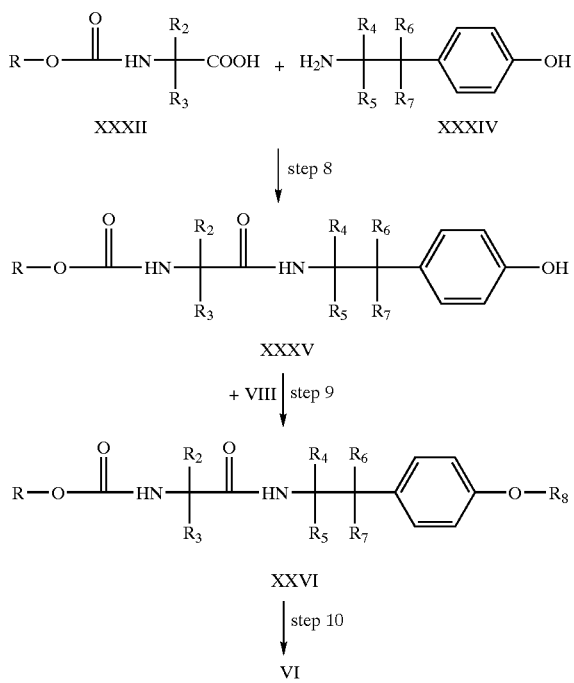

wherein R is lower alkyl or optionally substituted benzyl.

Step 8 is the amidation of an carbamate-protected amino acid of formula XXXIII with an amine of formula XXXIV. The reaction is performed in the same manner as described for step A.

Step 9 is the alkylation of a phenol of formula XXXV with an compound of formula VIII. The reaction is performed in the same manner as described for step D.

Step 10 is the hydrolysis of a carbamate of formula XXXVI. The reaction is performed in a solvent like hydrocarbons, e.g. toluene, like halogenated hydrocarbons, e.g. dichloromethane, like ketones, e.g. acetone, like esters, e.g. ethyl acetate, like ethers, e.g. dioxane or tetrahydrofuran, or like water or in mixtures of these solvents optionally in the presence of an organic acid like carboxylic acid, e.g. trifluoroacetic acid, or like a sulfonic acid, e.g. methanesulfonic acid or toluenesulfonic acid, or in the presence of an inorganic acid, e.g. hydrogen chloride or sulfuric acid, at temperatures ranging from −40° C. to +160° C.

The compounds of formula I are oils or solids at room temperature and are distinguished by valuable microbiocidal properties. They can be used in the agricultural sector or related technical fields preventively and curatively for the control of plant-destructive microorganisms. The compounds of formula I according to the invention are distinguished at low rates of concentration not only by outstanding microbiocidal, especially fungicida I, activity but also by being especially well tolerated by the treated crop plants.

Surprisingly, it has now been found that for practical purposes the compounds of formula I have a very advantageous biocidal spectrum in the control of phytopathogenic microorganisms, especially fungi. With the compounds of formula I it is possible to inhibit or destroy phytopathogenic microorganisms that occur on various crops of useful plants or on parts of such plants (fruit, blossom, leaves, stems, tubers, roots), while parts of the plants which grow later also remain protected, for example, against phyto pathogenic fungi.

The novel compounds of formula I prove to be effective against specific genera of the fungus classes Fungi imperfecti (e.g. *Cercospora*), *Basidio mycetes* (e.g. *Puccinia*) and *Ascomycetes* (e.g. *Erysiphe* and *Venturia*) and especially against *Oomycetes* (e.g. *Plasmopara, Peronospora, Pythium* and *Phytophthora*). They therefore represent in plant protection a valuable addition to the compositions for controlling phyto pathogenic fungi. The compounds of formula I can also be used as coatings or dressings for protecting seed (fruit, tubers, grains) and plant cuttings from fungal infections and against phyto pathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method of treating plants which is distinguished by the application of the novel compounds of formula I or of the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally used in the form of compositions and can be applied to the area or plant to be treated simultaneously or in succession with other active ingredients. Those other active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, resulting in some cases in unexpected synergistic activities.

Mixing components which are particularly preferred are azoles such as azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazole; pyrimidinyl carbinols, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph;

anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozolin; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, CGA 279202 (trifloxystrobin), picoxystrobin; dithiocarbamates, such as ferbam, mancozeb, maneb, metiram, propineb, thiram, zineb, ziram; N-halogenmethylthiophthalimides, such as captafol, captan, dichlofluanid, fluoromide, folpet, tolylfluanid; Cu compounds, such as Bordeaux mixture, copper hydroxide, copper oxychloride, copper sulfate, cuprous oxide, mancopper, oxine-copper; nitrophenol derivatives, such as dinocap, nitrothal-isopropyl; organo-P derivatives, such as edifenphos, iprobenphos, isoprothiolane, phosdiphen, pyrazophos, tolclofos-methyl; various, such as AC382042, acibenzolar-S-methyl, anilazine, blasticidin-S, quinomethionat, chloroneb, chlorothalonil, cymoxanil, dichlone, diclomezine, dicloran, diethofencarb, dimethomorph, dithianon, etridiazole, famoxadone, fenamidone, fenhexamid, fentin, ferimzone, fluazinam, flusulfamide, fosetyl-aluminium, hymexazol, IKF-916, iprovalicarb, kasugamycin, methasulfocarb, MON65500, pencycuron, phthalide, polyoxins, probenazole, propamocarb, pyroquilon, quinoxyfen, quintozene, RH-7281, RPA 407213, BAS 50001 F, sulfur, SYP-Z071, triazoxide, tricyclazole, triforine, validamycin.

Suitable carriers and surfactants may be solid or liquid and correspond to the substances ordinarily employed in formulation technology, such as e.g. natural or regenerated mineral substances, solvents, dispersants, wetting agents, tackifiers, thickeners, binders or fertilisers. Such carriers and additives are described, for example, in WO 95/30651.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the grains with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the compound(s) (active ingredient(s)) of formula I and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES FOR COMPOUNDS OF FORMULA I

Example A1.1

(S)-2-Ethanesulfonylamino-N-(2-{4-[3-(4-chloro-phenyl)-propargyloxy]-phenyl}-ethyl)-3-methyl-butyramide

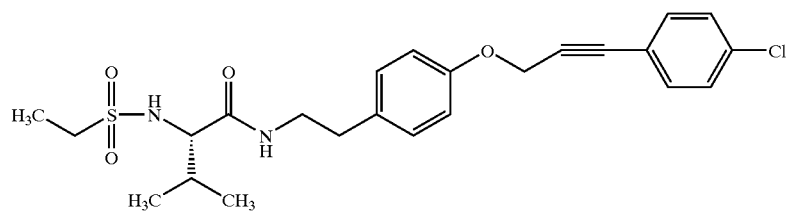

A mixture of 1.0 g of (S)-2-ethanesulfonylamino-N-[2-(4-hydroxy-phenyl)-ethyl]-3-methyl-butyramide, 1.3 g of toluene-4-sulfonic acid 3-(4-chloro-phenyl)-prop-2-ynyl ester and 4.9 ml of a 1M solution of sodium methoxide in methanol in 25 ml of methanol is heated to reflux for 2 hours. After cooling 200 ml of water is added. The mixture is extracted with ethyl acetate (2×300 ml). The organic layers are washed with brine (2×100 ml), combined, dried (MgSO$_4$) and evaporated. (S)-N-(2-{4-[3-(4-Chloro-phenyl)-propargyloxy]-phenyl}-ethyl)-2-ethanesulfonylamino-3-methyl-butyramide is obtained which is purified by recrystallization (ethyl acetate/hexane), m.p. 141–142° C.

Analogously to example A1.1 the compounds listed in table A1 are obtained.

*) Configuration on the α-C-atom in the amino acid moiety; Ph means phenyl

TABLE A1

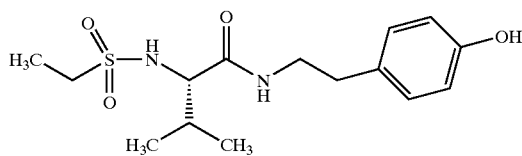

| No | $R_1$ | *) | $R_3$ | $R_4$ | $R_8$ | m.p. (° C.) |
|---|---|---|---|---|---|---|
| A1.1 | $CH_3$—$CH_2$— | (S) | $(CH_3)_2CH$— | H | (4-Cl—Ph)—C≡C—$CH_2$— | 141–142 |
| A1.2 | $CH_3$—$CH_2$— | (S) | $(CH_3)_2CH$— | H | (4-F—Ph)—C≡C—$CH_2$— | 133–134 |
| A1.3 | $CH_3$ | (S) | $(CH_3)_2CH$— | H | (4-Cl—Ph)—C≡C—$CH_2$— | 154–155 |
| A1.4 | $CH_3$ | (S) | $(CH_3)_2CH$— | H | (4-F—Ph)—C≡C—$CH_2$— | 104–105 |
| A1.5 | $CH_3$ | (S) | $(CH_3)_2CH$— | H | (4-Br—Ph)—C≡C—$CH_2$— | 161–164 |
| A1.6 | $CH_3$ | (S) | $(CH_3)_2CH$— | H | (4-$CH_3$-Ph)—C≡C—$CH_2$— | 110–112 |
| A1.7 | $CH_3$ | (S) | $(CH_3)_2CH$— | H | (4-Cl—Ph)—CH=CH—$CH_2$— | 144–145 |
| A1.8 | $CH_3$ | (S) | $(CH_3)_2CH$— | H | (4-Cl—Ph)—$CH_2$—$CH_2$—$CH_2$— | 176–177 |
| A1.9 | $CH_3$ | (S) | $(CH_3)_2CH$— | H | (3-$CF_3$—Ph)—$CH_2$ | 147–153 |

Example A2.1

(S)-2-Ethanesulfonylamino-N-[2-(4-hydroxy-phenyl)-ethyl]-3-methyl-butyramide 18.6 g of (S)-N-[2-(4-benzyloxy-phenyl)-ethyl]-2-ethanesulfonylamino-3-methyl-butyramide and 16.8 g of palladium (5% on charcoal) in 400 ml of tetrahydrofuran are shaken under a hydrogen atmosphere at +30 to +−35° C. and at normal pressure for 5 hours. The reaction mixture is filtered and evaporated. (S)-2-ethanesulfonylamino-N-[2-(4-hydroxy-phenyl)-ethyl]-3-methyl-butyramide is obtained in form of an oil [MS (m/e): 329 (M+H)$^+$].

Analogously to example A2.1 the compounds listed in table A2 are obtained.

*) Configuration on the α-C-atom in the amino acid moiety; Ph means phenyl

TABLE A2

| No | $R_1$ | *) | $R_3$ | $R_4$ | m.p. (° C.) |
|---|---|---|---|---|---|
| A2.1 | $CH_3$—$CH_2$— | (S) | $(CH_3)_2CH$— | H | Oil |
| A2.2 | $CH_3$ | (S) | $(CH_3)_2CH$— | H | 120–121 |

*) Configuration of the amino acid moiety

Example A3.1

(S)-N-[2-(4-Benzyloxy-phenyl)-ethyl]-2-ethanesulfonylamino-3-methyl-butyramide 15 g of (S)-2-ethanesulfonylamino-3-methyl-butyric acid, 10.3 g of thionyl chloride and N,N-dimethylformamide (2 drops) in toluene (75 ml) are refluxed for 2 hours. The solvent is then evaporated. To the resulting residue 100 ml of toluene is added. The mixture is then evaporated to dryness again. The residue is dissolved in dioxane (100 ml) and added to a mixture of 2-(4-benzyloxy-phenyl)-ethylamine (15.3 g) and triethylamine (7.2 g) in dioxane (100 ml). The reaction mixture is stirred at room temperature over night. Water (400 ml) is added. It is extracted with ethyl acetate (2×500 ml). The organic layers are washed with hydrochloric acid (80 ml, 1M solution) and brine (2×100 ml), dried (MgSO$_4$) and evaporated. (S)-N-[2-(4-Benzyloxy-phenyl)-ethyl]-2-ethanesulfonylamino-3-methyl-butyramide which is purified by recrystallization (ethyl acetate/hexane), m.p. 133–134° C.

Analogously to example A3.1 the compounds listed in table A3 are obtained.

*) Configuration on the α-C-atom in the amino acid moiety; Ph means phenyl

TABLE A3

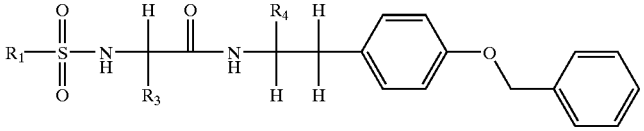

| No | $R_1$ | *) | $R_3$ | $R_4$ | m.p. (° C.) |
|---|---|---|---|---|---|
| A3.1 | CH₃—CH₂— | (S) | (CH₃)₂CH— | H | 133–134 |
| A3.2 | CH₃ | (S) | (CH₃)₂CH— | H | 153–154 |

*) Configuration of the amino acid moiety

Analogously to the above Examples the following compounds of Tables 1 to 13 may be prepared. In the tables Ph means phenyl.

TABLE 1

Compounds represented by the Formula I.1 where the combination of the groups $R_1$, $R_3$ and $R_8$ corresponds to each row in table A.

I.1
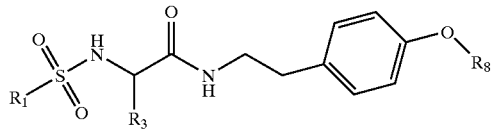

TABLE 2

Compounds represented by the Formula I.2 where the combination of the groups $R_1$, $R_3$ and $R_8$ corresponds to each row in table A.

I.2
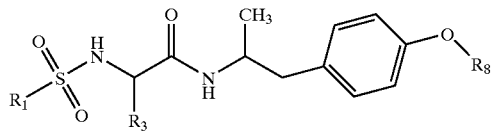

TABLE 3

Compounds represented by the Formula I.3 where the combination of the groups $R_1$, $R_3$ and $R_8$ corresponds to each row in table A.

I.3
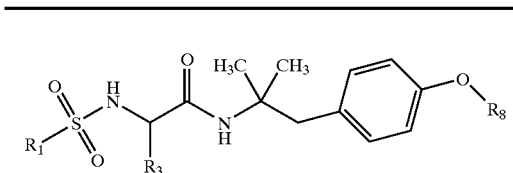

TABLE 4

Compounds represented by the Formula I.4 where the combination of the groups $R_1$, $R_3$ and $R_8$ corresponds to each row in table A.

I.4
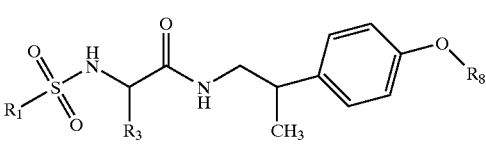

TABLE 5

Compounds represented by the Formula I.5 where the combination of the groups $R_1$, $R_3$ and $R_8$ corresponds to each row in table A.

I.5
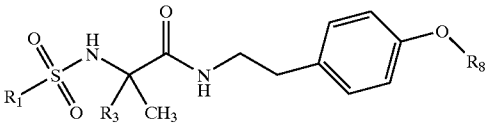

TABLE 6

Compounds represented by the Formula I.6 where the combination of the groups $R_1$, $R_3$ and $R_8$ corresponds to each row in table A.

I.6
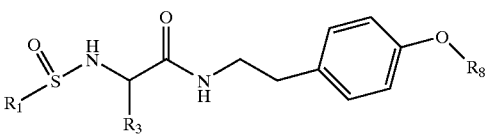

TABLE A

| No. | R₁ | R₃ | R₈ |
|---|---|---|---|
| 001 | $CH_3-$ | $CH_3-CH_2-$ | $CH_3-(CH_2)_3-C\equiv C-CH_2-$ |
| 002 | $CH_3-CH_2-$ | $CH_3-CH_2-$ | $CH_3-(CH_2)_3-C\equiv C-CH_2-$ |
| 003 | $(CH_3)_2N-$ | $CH_3-CH_2-$ | $CH_3-(CH_2)_3-C\equiv C-CH_2-$ |
| 004 | $CH_3-CH_2-CH_2-$ | $CH_3-CH_2-$ | $CH_3-(CH_2)_3-C\equiv C-CH_2-$ |
| 005 | $(CH_3)_2CH-$ | $CH_3-CH_2-$ | $CH_3-(CH_2)_3-C\equiv C-CH_2-$ |
| 006 | $Cl-CH_2-CH_2-CH_2-$ | $CH_3-CH_2-$ | $CH_3-(CH_2)_3-C\equiv C-CH_2-$ |
| 007 | $CH_3-$ | $(CH_3)_2CH-$ | $CH_3-(CH_2)_3-C\equiv C-CH_2-$ |
| 008 | $CH_3-CH_2-$ | $(CH_3)_2CH-$ | $CH_3-(CH_2)_3-C\equiv C-CH_2-$ |
| 009 | $(CH_3)_2N-$ | $(CH_3)_2CH-$ | $CH_3-(CH_2)_3-C\equiv C-CH_2-$ |
| 010 | $CH_3-CH_2-CH_2-$ | $(CH_3)_2CH-$ | $CH_3-(CH_2)_3-C\equiv C-CH_2-$ |
| 011 | $(CH_3)_2CH-$ | $(CH_3)_2CH-$ | $CH_3-(CH_2)_3-C\equiv C-CH_2-$ |
| 012 | $Cl-CH_2-CH_2-CH_2-$ | $(CH_3)_2CH-$ | $CH_3-(CH_2)_3-C\equiv C-CH_2-$ |
| 013 | $CH_3-$ | $CH_3-CH_2-CH_2-$ | $CH_3-(CH_2)_3-C\equiv C-CH_2-$ |
| 014 | $CH_3-CH_2-$ | $CH_3-CH_2-CH_2-$ | $CH_3-(CH_2)_3-C\equiv C-CH_2-$ |
| 015 | $(CH_3)_2N-$ | $CH_3-CH_2-CH_2-$ | $CH_3-(CH_2)_3-C\equiv C-CH_2-$ |
| 016 | $CH_3-CH_2-CH_2-$ | $CH_3-CH_2-CH_2-$ | $CH_3-(CH_2)_3-C\equiv C-CH_2-$ |
| 017 | $(CH_3)_2CH-$ | $CH_3-CH_2-CH_2-$ | $CH_3-(CH_2)_3-C\equiv C-CH_2-$ |
| 018 | $Cl-CH_2-CH_2-CH_2-$ | $CH_3-CH_2-CH_2-$ | $CH_3-(CH_2)_3-C\equiv C-CH_2-$ |
| 019 | $CH_3-$ | cyclopropyl-$CH-$ | $CH_3-(CH_2)_3-C\equiv C-CH_2-$ |
| 020 | $CH_3-CH_2-$ | cyclopropyl-$CH-$ | $CH_3-(CH_2)_3-C\equiv C-CH_2-$ |
| 021 | $(CH_3)_2N-$ | cyclopropyl-$CH-$ | $CH_3-(CH_2)_3-C\equiv C-CH_2-$ |
| 022 | $CH_3-CH_2-CH_2-$ | cyclopropyl-$CH-$ | $CH_3-(CH_2)_3-C\equiv C-CH_2-$ |
| 023 | $(CH_3)_2CH-$ | cyclopropyl-$CH-$ | $CH_3-(CH_2)_3-C\equiv C-CH_2-$ |
| 024 | $Cl-CH_2-CH_2-CH_2-$ | cyclopropyl-$CH-$ | $CH_3-(CH_2)_3-C\equiv C-CH_2-$ |
| 025 | $CH_3-$ | $CH_2=CH-CH_2-$ | $CH_3-(CH_2)_3-C\equiv C-CH_2-$ |
| 026 | $CH_3-CH_2-$ | $CH_2=CH-CH_2-$ | $CH_3-(CH_2)_3-C\equiv C-CH_2-$ |
| 027 | $(CH_3)_2N-$ | $CH_2=CH-CH_2-$ | $CH_3-(CH_2)_3-C\equiv C-CH_2-$ |
| 028 | $CH_3-CH_2-CH_2-$ | $CH_2=CH-CH_2-$ | $CH_3-(CH_2)_3-C\equiv C-CH_2-$ |
| 029 | $(CH_3)_2CH-$ | $CH_2=CH-CH_2-$ | $CH_3-(CH_2)_3-C\equiv C-CH_2-$ |
| 030 | $Cl-CH_2-CH_2-CH_2-$ | $CH_2=CH-CH_2-$ | $CH_3-(CH_2)_3-C\equiv C-CH_2-$ |
| 031 | $CH_3-$ | $CH\equiv C-CH_2-$ | $CH_3-(CH_2)_3-C\equiv C-CH_2-$ |
| 032 | $CH_3-CH_2-$ | $CH\equiv C-CH_2-$ | $CH_3-(CH_2)_3-C\equiv C-CH_2-$ |
| 033 | $(CH_3)_2N-$ | $CH\equiv C-CH_2-$ | $CH_3-(CH_2)_3-C\equiv C-CH_2-$ |
| 034 | $CH_3-CH_2-CH_2-$ | $CH\equiv C-CH_2-$ | $CH_3-(CH_2)_3-C\equiv C-CH_2-$ |
| 035 | $(CH_3)_2CH-$ | $CH\equiv C-CH_2-$ | $CH_3-(CH_2)_3-C\equiv C-CH_2-$ |
| 036 | $Cl-CH_2-CH_2-CH_2-$ | $CH\equiv C-CH_2-$ | $CH_3-(CH_2)_3-C\equiv C-CH_2-$ |
| 037 | $CH_3-$ | $CH_3-CH_2-CH(CH_3)-$ | $CH_3-(CH_2)_3-C\equiv C-CH_2-$ |
| 038 | $CH_3-CH_2-$ | $CH_3-CH_2-CH(CH_3)-$ | $CH_3-(CH_2)_3-C\equiv C-CH_2-$ |
| 039 | $(CH_3)_2N-$ | $CH_3-CH_2-CH(CH_3)-$ | $CH_3-(CH_2)_3-C\equiv C-CH_2-$ |
| 040 | $CH_3-CH_2-CH_2-$ | $CH_3-CH_2-CH(CH_3)-$ | $CH_3-(CH_2)_3-C\equiv C-CH_2-$ |
| 041 | $(CH_3)_2CH-$ | $CH_3-CH_2-CH(CH_3)-$ | $CH_3-(CH_2)_3-C\equiv C-CH_2-$ |
| 042 | $Cl-CH_2-CH_2-CH_2-$ | $CH_3-CH_2-CH(CH_3)-$ | $CH_3-(CH_2)_3-C\equiv C-CH_2-$ |
| 045 | $CH_3-$ | $CH_3-CH_2-$ | cyclopropyl-$C\equiv C-CH_2-$ |
| 046 | $CH_3-CH_2-$ | $CH_3-CH_2-$ | cyclopropyl-$C\equiv C-CH_2-$ |
| 047 | $(CH_3)_2N-$ | $CH_3-CH_2-$ | cyclopropyl-$C\equiv C-CH_2-$ |
| 048 | $CH_3-CH_2-CH_2-$ | $CH_3-CH_2-$ | cyclopropyl-$C\equiv C-CH_2-$ |
| 049 | $(CH_3)_2CH-$ | $CH_3-CH_2-$ | cyclopropyl-$C\equiv C-CH_2-$ |

TABLE A-continued
| No. | R₁ | R₃ | R₈ |
|---|---|---|---|
| 050 | Cl—CH₂—CH₂—CH₂— | CH₃—CH₂— | 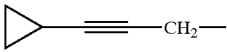 |
| 51 | CH₃— | (CH₃)₂CH— | 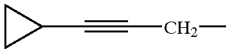 |
| 052 | CH₃—CH₂— | (CH₃)₂CH— | 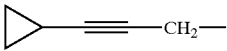 |
| 053 | (CH₃)₂N— | (CH₃)₂CH— | 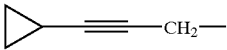 |
| 054 | CH₃—CH₂—CH₂— | (CH₃)₂CH— |  |
| 055 | (CH₃)₂CH— | (CH₃)₂CH— | 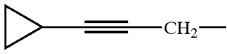 |
| 056 | Cl—CH₂—CH₂—CH₂— | (CH₃)₂CH— | 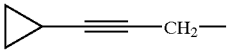 |
| 057 | CH₃— | CH₃—CH₂—CH₂— | 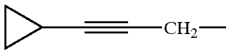 |
| 058 | CH₃—CH₂— | CH₃—CH₂—CH₂— | 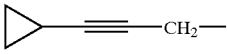 |
| 059 | (CH₃)₂N— | CH₃—CH₂—CH₂— | 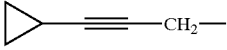 |
| 060 | CH₃—CH₂—CH₂— | CH₃—CH₂—CH₂— | 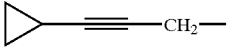 |
| 061 | (CH₃)₂CH— | CH₃—CH₂—CH₂— | 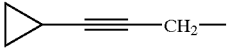 |
| 062 | Cl—CH₂—CH₂—CH₂— | CH₃—CH₂—CH₂— | 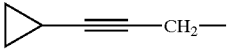 |
| 063 | CH₃— |  | 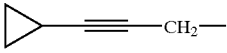 |
| 064 | CH₃—CH₂— |  | 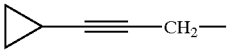 |
| 065 | (CH₃)₂N— |  | 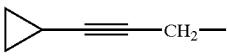 |
| 066 | CH₃—CH₂—CH₂— |  | 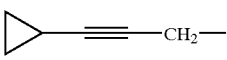 |
| 067 | (CH₃)₂CH— |  |  |
| 068 | Cl—CH₂—CH₂—CH₂— |  |  |
| 069 | CH₃— | CH₂=CH—CH₂— |  |
| 070 | CH₃—CH₂— | CH₂=CH—CH₂— |  |
| 071 | (CH₃)₂N— | CH₂=CH—CH₂— |  |

TABLE A-continued

| No. | R₁ | R₃ | R₈ |
|---|---|---|---|
| 072 | CH₃—CH₂—CH₂— | CH₂=CH—CH₂— | 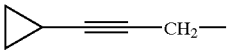—CH₂— |
| 073 | (CH₃)₂CH— | CH₂=CH—CH₂— | —CH₂— |
| 074 | Cl—CH₂—CH₂—CH₂— | CH₂=CH—CH₂— | —CH₂— |
| 075 | CH₃— | CH≡C—CH₂— | —CH₂— |
| 076 | CH₃—CH₂— | CH≡C—CH₂— | —CH₂— |
| 077 | (CH₃)₂N— | CH≡C—CH₂— | —CH₂— |
| 078 | CH₃—CH₂—CH₂— | CH≡C—CH₂— | 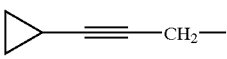—CH₂— |
| 079 | (CH₃)₂CH— | CH≡C—CH₂— | 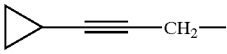—CH₂— |
| 080 | Cl—CH₂—CH₂—CH₂— | CH≡C—CH₂— | 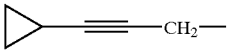—CH₂— |
| 081 | CH₃— | CH₃—CH₂—CH(CH₃)— | 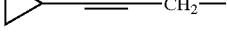—CH₂— |
| 082 | CH₃—CH₂— | CH₃—CH₂—CH(CH₃)— | —CH₂— |
| 083 | (CH₃)₂N— | CH₃—CH₂—CH(CH₃)— | —CH₂— |
| 084 | CH₃—CH₂—CH₂— | CH₃—CH₂—CH(CH₃)— | —CH₂— |
| 085 | (CH₃)₂CH— | CH₃—CH₂—CH(CH₃)— | 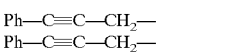—CH₂— |
| 086 | Cl—CH₂—CH₂—CH₂— | CH₃—CH₂—CH(CH₃)— | 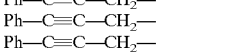—CH₂— |
| 087 | CH₃— | CH₃—CH₂— | Ph—C≡C—CH₂— |
| 088 | CH₃—CH₂— | CH₃—CH₂— | Ph—C≡C—CH₂— |
| 089 | (CH₃)₂N— | CH₃—CH₂— | Ph—C≡C—CH₂— |
| 090 | CH₃—CH₂—CH₂— | CH₃—CH₂— | Ph—C≡C—CH₂— |
| 091 | (CH₃)₂CH— | CH₃—CH₂— | Ph—C≡C—CH₂— |
| 092 | Cl—CH₂—CH₂—CH₂— | CH₃—CH₂— | Ph—C≡C—CH₂— |
| 093 | CH₃— | (CH₃)₂CH— | Ph—C≡C—CH₂— |
| 094 | CH₃—CH₂— | (CH₃)₂CH— | Ph—C≡C—CH₂— |
| 095 | (CH₃)₂N— | (CH₃)₂CH— | Ph—C≡C—CH₂— |
| 096 | CH₃—CH₂—CH₂— | (CH₃)₂CH— | Ph—C≡C—CH₂— |
| 097 | (CH₃)₂CH— | (CH₃)₂CH— | Ph—C≡C—CH₂— |
| 098 | Cl—CH₂—CH₂—CH₂— | (CH₃)₂CH— | Ph—C≡C—CH₂— |
| 099 | CH₃— | CH₃—CH₂—CH₂— | Ph—C≡C—CH₂— |
| 100 | CH₃—CH₂— | CH₃—CH₂—CH₂— | Ph—C≡C—CH₂— |
| 101 | (CH₃)₂N— | CH₃—CH₂—CH₂— | Ph—C≡C—CH₂— |
| 102 | CH₃—CH₂—CH₂— | CH₃—CH₂—CH₂— | Ph—C≡C—CH₂— |
| 103 | (CH₃)₂CH— | CH₃—CH₂—CH₂— | Ph—C≡C—CH₂— |
| 104 | Cl—CH₂—CH₂—CH₂— | CH₃—CH₂—CH₂— | Ph—C≡C—CH₂— |
| 105 | CH₃— | CH— | Ph—C≡C—CH₂— |

TABLE A-continued

| No. | R₁ | R₃ | R₈ |
|-----|-----|-----|-----|
| 106 | CH₃—CH₂— | CH— | Ph—C≡C—CH₂— |
| 107 | (CH₃)₂N— | CH— | Ph—C≡C—CH₂— |
| 108 | CH₃—CH₂—CH₂— | CH— | Ph—C≡C—CH₂— |
| 109 | (CH₃)₂CH— | CH— | Ph—C≡C—CH₂— |
| 110 | Cl—CH₂—CH₂—CH₂— | CH— | Ph—C≡C—CH₂— |
| 111 | CH₃— | CH₂=CH—CH₂— | Ph—C≡C—CH₂— |
| 112 | CH₃—CH₂— | CH₂=CH—CH₂— | Ph—C≡C—CH₂— |
| 113 | (CH₃)₂N— | CH₂=CH—CH₂— | Ph—C≡C—CH₂— |
| 114 | CH₃—CH₂—CH₂— | CH₂=CH—CH₂— | Ph—C≡C—CH₂— |
| 115 | (CH₃)₂CH— | CH₂=CH—CH₂— | Ph—C≡C—CH₂— |
| 116 | Cl—CH₂—CH₂—CH₂— | CH₂=CH—CH₂— | Ph—C≡C—CH₂— |
| 117 | CH₃— | CH≡C—CH₂— | Ph—C≡C—CH₂— |
| 118 | CH₃—CH₂— | CH≡C—CH₂— | Ph—C≡C—CH₂— |
| 119 | (CH₃)₂N— | CH≡C—CH₂— | Ph—C≡C—CH₂— |
| 120 | CH₃—CH₂—CH₂— | CH≡C—CH₂— | Ph—C≡C—CH₂— |
| 121 | (CH₃)₂CH— | CH≡C—CH₂— | Ph—C≡C—CH₂— |
| 122 | Cl—CH₂—CH₂—CH₂— | CH≡C—CH₂— | Ph—C≡C—CH₂— |
| 123 | CH₃— | CH₃—CH₂—CH(CH₃)— | Ph—C≡C—CH₂— |
| 124 | CH₃—CH₂— | CH₃—CH₂—CH(CH₃)— | Ph—C≡C—CH₂— |
| 125 | (CH₃)₂N— | CH₃—CH₂—CH(CH₃)— | Ph—C≡C—CH₂— |
| 126 | CH₃—CH₂—CH₂— | CH₃—CH₂—CH(CH₃)— | Ph—C≡C—CH₂— |
| 127 | (CH₃)₂CH— | CH₃—CH₂—CH(CH₃)— | Ph—C≡C—CH₂— |
| 128 | Cl—CH₂—CH₂—CH₂— | CH₃—CH₂—CH(CH₃)— | Ph—C≡C—CH₂— |
| 129 | CH₃— | CH₃—CH₂— | (4-F—Ph)—C≡C—CH₂— |
| 130 | CH₃—CH₂— | CH₃—CH₂— | (4-F—Ph)—C≡C—CH₂— |
| 131 | (CH₃)₂N— | CH₃—CH₂— | (4-F—Ph)—C≡C—CH₂— |
| 132 | CH₃—CH₂—CH₂— | CH₃—CH₂— | (4-F—Ph)—C≡C—CH₂— |
| 133 | (CH₃)₂CH— | CH₃—CH₂— | (4-F—Ph)—C≡C—CH₂— |
| 134 | Cl—CH₂—CH₂—CH₂— | CH₃—CH₂— | (4-F—Ph)—C≡C—CH₂— |
| 135 | CH₃— | (CH₃)₂CH₂— | (4-F—Ph)—C≡C—CH₂— |
| 136 | CH₃—CH₂— | (CH₃)₂CH₂— | (4-F—Ph)—C≡C—CH₂— |
| 137 | (CH₃)₂N— | (CH₃)₂CH₂— | (4-F—Ph)—C≡C—CH₂— |
| 138 | CH₃—CH₂—CH₂— | (CH₃)₂CH₂— | (4-F—Ph)—C≡C—CH₂— |
| 139 | (CH₃)₂CH— | (CH₃)₂CH₂— | (4-F—Ph)—C≡C—CH₂— |
| 140 | Cl—CH₂—CH₂—CH₂— | (CH₃)₂CH₂— | (4-F—Ph)—C≡C—CH₂— |
| 141 | CH₃— | CH₃—CH₂—CH₂— | (4-F—Ph)—C≡C—CH₂— |
| 142 | CH₃—CH₂— | CH₃—CH₂—CH₂— | (4-F—Ph)—C≡C—CH₂— |
| 143 | (CH₃)₂N— | CH₃—CH₂—CH₂— | (4-F—Ph)—C≡C—CH₂— |
| 144 | CH₃—CH₂—CH₂— | CH₃—CH₂—CH₂— | (4-F—Ph)—C≡C—CH₂— |
| 145 | (CH₃)₂CH— | CH₃—CH₂—CH₂— | (4-F—Ph)—C≡C—CH₂— |
| 146 | Cl—CH₂—CH₂—CH₂— | CH₃—CH₂—CH₂— | (4-F—Ph)—C≡C—CH₂— |
| 147 | CH₃— | CH— | (4-F—Ph)—C≡C—CH₂— |
| 148 | CH₃—CH₂— | CH— | (4-F—Ph)—C≡C—CH₂— |
| 149 | (CH₃)₂N— | CH— | (4-F—Ph)—C≡C—CH₂— |
| 150 | CH₃—CH₂—CH₂— | CH— | (4-F—Ph)—C≡C—CH₂— |
| 151 | (CH₃)₂CH— | CH— | (4-F—Ph)—C≡C—CH₂— |
| 152 | Cl—CH₂—CH₂—CH₂— | CH— | (4-F—Ph)—C≡C—CH₂— |
| 153 | CH₃— | CH₂=CH—CH₂— | (4-F—Ph)—C≡C—CH₂— |

TABLE A-continued

| No. | R₁ | R₃ | R₈ |
|---|---|---|---|
| 154 | CH₃—CH₂— | CH₂=CH—CH₂— | (4-F—Ph)—C≡C—CH₂— |
| 155 | (CH₃)₂N— | CH₂=CH—CH₂— | (4-F—Ph)—C≡C—CH₂— |
| 156 | CH₃—CH₂—CH₂— | CH₂=CH—CH₂— | (4-F—Ph)—C≡C—CH₂— |
| 157 | (CH₃)₂CH— | CH₂=CH—CH₂— | (4-F—Ph)—C≡C—CH₂— |
| 158 | Cl—CH₂—CH₂—CH₂— | CH₂=CH—CH₂— | (4-F—Ph)—C≡C—CH₂— |
| 159 | CH₃— | CH≡C—CH₂— | (4-F—Ph)—C≡C—CH₂— |
| 160 | CH₃—CH₂— | CH≡C—CH₂— | (4-F—Ph)—C≡C—CH₂— |
| 161 | (CH₃)₂N— | CH≡C—CH₂— | (4-F—Ph)—C≡C—CH₂— |
| 162 | CH₃—CH₂—CH₂— | CH≡C—CH₂— | (4-F—Ph)—C≡C—CH₂— |
| 163 | (CH₃)₂CH— | CH≡C—CH₂— | (4-F—Ph)—C≡C—CH₂— |
| 164 | Cl—CH₂—CH₂—CH₂— | CH≡C—CH₂— | (4-F—Ph)—C≡C—CH₂— |
| 165 | CH₃— | CH₃—CH₂—CH(CH₃)— | (4-F—Ph)—C≡C—CH₂— |
| 166 | CH₃—CH₂— | CH₃—CH₂—CH(CH₃)— | (4-F—Ph)—C≡C—CH₂— |
| 167 | (CH₃)₂N— | CH₃—CH₂—CH(CH₃)— | (4-F—Ph)—C≡C—CH₂— |
| 168 | CH₃—CH₂—CH₂— | CH₃—CH₂—CH(CH₃)— | (4-F—Ph)—C≡C—CH₂— |
| 169 | (CH₃)₂CH— | CH₃—CH₂—CH(CH₃)— | (4-F—Ph)—C≡C—CH₂— |
| 170 | Cl—CH₂—CH₂—CH₂— | CH₃—CH₂—CH(CH₃)— | (4-F—Ph)—C≡C—CH₂— |
| 171 | CH₃— | CH₃—CH₂— | (4-Cl—Ph)—C≡C—CH₂— |
| 172 | CH₃—CH₂— | CH₃—CH₂— | (4-Cl—Ph)—C≡C—CH₂— |
| 173 | (CH₃)₂N— | CH₃—CH₂— | (4-Cl—Ph)—C≡C—CH₂— |
| 174 | CH₃—CH₂—CH₂— | CH₃—CH₂— | (4-Cl—Ph)—C≡C—CH₂— |
| 175 | (CH₃)₂CH— | CH₃—CH₂— | (4-Cl—Ph)—C≡C—CH₂— |
| 176 | Cl—CH₂—CH₂—CH₂— | CH₃—CH₂— | (4-Cl—Ph)—C≡C—CH₂— |
| 177 | CH₃— | (CH₃)₂CH— | (4-Cl—Ph)—C≡C—CH₂— |
| 178 | CH₃—CH₂— | (CH₃)₂CH— | (4-Cl—Ph)—C≡C—CH₂— |
| 179 | (CH₃)₂N— | (CH₃)₂CH— | (4-Cl—Ph)—C≡C—CH₂— |
| 180 | CH₃—CH₂—CH₂— | (CH₃)₂CH— | (4-Cl—Ph)—C≡C—CH₂— |
| 181 | (CH₃)₂CH— | (CH₃)₂CH— | (4-Cl—Ph)—C≡C—CH₂— |
| 182 | Cl—CH₂—CH₂—CH₂— | (CH₃)₂CH— | (4-Cl—Ph)—C≡C—CH₂— |
| 183 | CH₃— | CH₃—CH₂—CH₂— | (4-Cl—Ph)—C≡C—CH₂— |
| 184 | CH₃—CH₂— | CH₃—CH₂—CH₂— | (4-Cl—Ph)—C≡C—CH₂— |
| 185 | (CH₃)₂N— | CH₃—CH₂—CH₂— | (4-Cl—Ph)—C≡C—CH₂— |
| 186 | CH₃—CH₂—CH₂— | CH₃—CH₂—CH₂— | (4-Cl—Ph)—C≡C—CH₂— |
| 187 | (CH₃)₂CH— | CH₃—CH₂—CH₂— | (4-Cl—Ph)—C≡C—CH₂— |
| 188 | Cl—CH₂—CH₂—CH₂— | CH₃—CH₂—CH₂— | (4-Cl—Ph)—C≡C—CH₂— |
| 189 | CH₃— | ▷CH— | (4-Cl—Ph)—C≡C—CH₂— |
| 190 | CH₃—CH₂— | ▷CH— | (4-Cl—Ph)—C≡C—CH₂— |
| 191 | (CH₃)₂N— | ▷CH— | (4-Cl—Ph)—C≡C—CH₂— |
| 192 | CH₃—CH₂—CH₂— | ▷CH— | (4-Cl—Ph)—C≡C—CH₂— |
| 193 | (CH₃)₂CH— | ▷CH— | (4-Cl—Ph)—C≡C—CH₂— |
| 194 | Cl—CH₂—CH₂—CH₂— | ▷CH— | (4-Cl—Ph)—C≡C—CH₂— |
| 195 | CH₃— | CH₂=CH—CH₂— | (4-Cl—Ph)—C≡C—CH₂— |
| 196 | CH₃—CH₂— | CH₂=CH—CH₂— | (4-Cl—Ph)—C≡C—CH₂— |
| 197 | (CH₃)₂N— | CH₂=CH—CH₂— | (4-Cl—Ph)—C≡C—CH₂— |
| 198 | CH₃—CH₂—CH₂— | CH₂=CH—CH₂— | (4-Cl—Ph)—C≡C—CH₂— |
| 199 | (CH₃)₂CH— | CH₂=CH—CH₂— | (4-Cl—Ph)—C≡C—CH₂— |
| 200 | Cl—CH₂—CH₂—CH₂— | CH₂=CH—CH₂— | (4-Cl—Ph)—C≡C—CH₂— |
| 201 | CH₃— | CH≡C—CH₂— | (4-Cl—Ph)—C≡C—CH₂— |
| 202 | CH₃—CH₂— | CH≡C—CH₂— | (4-Cl—Ph)—C≡C—CH₂— |
| 203 | (CH₃)₂N— | CH≡C—CH₂— | (4-Cl—Ph)—C≡C—CH₂— |
| 204 | CH₃—CH₂—CH₂— | CH≡C—CH₂— | (4-Cl—Ph)—C≡C—CH₂— |
| 205 | (CH₃)₂CH— | CH≡C—CH₂— | (4-Cl—Ph)—C≡C—CH₂— |
| 206 | Cl—CH₂—CH₂—CH₂— | CH≡C—CH₂— | (4-Cl—Ph)—C≡C—CH₂— |
| 207 | CH₃— | CH₃—CH₂—CH(CH₃)— | (4-Cl—Ph)—C≡C—CH₂— |
| 208 | CH₃—CH₂— | CH₃—CH₂—CH(CH₃)— | (4-Cl—Ph)—C≡C—CH₂— |
| 209 | (CH₃)₂N— | CH₃—CH₂—CH(CH₃)— | (4-Cl—Ph)—C≡C—CH₂— |
| 210 | CH₃—CH₂—CH₂— | CH₃—CH₂—CH(CH₃)— | (4-Cl—Ph)—C≡C—CH₂— |
| 211 | (CH₃)₂CH— | CH₃—CH₂—CH(CH₃)— | (4-Cl—Ph)—C≡C—CH₂— |
| 212 | Cl—CH₂—CH₂—CH₂— | CH₃—CH₂—CH(CH₃)— | (4-Cl—Ph)—C≡C—CH₂— |
| 213 | CH₃— | CH₃—CH₂— | (4-Br—Ph)—C≡C—CH₂— |

TABLE A-continued

| No. | R₁ | R₃ | R₈ |
|---|---|---|---|
| 214 | CH₃—CH₂— | CH₃—CH₂— | (4-Br—Ph)—C≡C—CH₂— |
| 215 | (CH₃)₂N— | CH₃—CH₂— | (4-Br—Ph)—C≡C—CH₂— |
| 216 | CH₃—CH₂—CH₂— | CH₃—CH₂— | (4-Br—Ph)—C≡C—CH₂— |
| 217 | (CH₃)₂CH— | CH₃—CH₂— | (4-Br—Ph)—C≡C—CH₂— |
| 218 | Cl—CH₂—CH₂—CH₂— | CH₃—CH₂— | (4-Br—Ph)—C≡C—CH₂— |
| 219 | CH₃— | (CH₃)₂CH— | (4-Br—Ph)—C≡C—CH₂— |
| 220 | CH₃—CH₂— | (CH₃)₂CH— | (4-Br—Ph)—C≡C—CH₂— |
| 221 | (CH₃)₂N— | (CH₃)₂CH— | (4-Br—Ph)—C≡C—CH₂— |
| 222 | CH₃—CH₂—CH₂— | (CH₃)₂CH— | (4-Br—Ph)—C≡C—CH₂— |
| 223 | (CH₃)₂CH— | (CH₃)₂CH— | (4-Br—Ph)—C≡C—CH₂— |
| 224 | Cl—CH₂—CH₂—CH₂— | (CH₃)₂CH— | (4-Br—Ph)—C≡C—CH₂— |
| 225 | CH₃— | CH₃—CH₂—CH₂— | (4-Br—Ph)—C≡C—CH₂— |
| 226 | CH₃—CH₂— | CH₃—CH₂—CH₂— | (4-Br—Ph)—C≡C—CH₂— |
| 227 | (CH₃)₂N— | CH₃—CH₂—CH₂— | (4-Br—Ph)—C≡C—CH₂— |
| 228 | CH₃—CH₂—CH₂— | CH₃—CH₂—CH₂— | (4-Br—Ph)—C≡C—CH₂— |
| 229 | (CH₃)₂CH— | CH₃—CH₂—CH₂— | (4-Br—Ph)—C≡C—CH₂— |
| 230 | Cl—CH₂—CH₂—CH₂— | CH₃—CH₂—CH₂— | (4-Br—Ph)—C≡C—CH₂— |
| 231 | CH₃— |  | (4-Br—Ph)—C≡C—CH₂— |
| 232 | CH₃—CH₂— |  | (4-Br—Ph)—C≡C—CH₂— |
| 233 | (CH₃)₂N— |  | (4-Br—Ph)—C≡C—CH₂— |
| 234 | CH₃—CH₂—CH₂— |  | (4-Br—Ph)—C≡C—CH₂— |
| 235 | (CH₃)₂CH— |  | (4-Br—Ph)—C≡C—CH₂— |
| 236 | Cl—CH₂—CH₂—CH₂— |  | (4-Br—Ph)—C≡C—CH₂— |
| 237 | CH₃— | CH₂=CH—CH₂— | (4-Br—Ph)—C≡C—CH₂— |
| 238 | CH₃—CH₂— | CH₂=CH—CH₂— | (4-Br—Ph)—C≡C—CH₂— |
| 239 | (CH₃)₂N— | CH₂=CH—CH₂— | (4-Br—Ph)—C≡C—CH₂— |
| 240 | CH₃—CH₂—CH₂— | CH₂=CH—CH₂— | (4-Br—Ph)—C≡C—CH₂— |
| 241 | (CH₃)₂CH— | CH₂=CH—CH₂— | (4-Br—Ph)—C≡C—CH₂— |
| 242 | Cl—CH₂—CH₂—CH₂— | CH₂=CH—CH₂— | (4-Br—Ph)—C≡C—CH₂— |
| 243 | CH₃— | CH≡C—CH₂— | (4-Br—Ph)—C≡C—CH₂— |
| 244 | CH₃—CH₂— | CH≡C—CH₂— | (4-Br—Ph)—C≡C—CH₂— |
| 245 | (CH₃)₂N— | CH≡C—CH₂— | (4-Br—Ph)—C≡C—CH₂— |
| 246 | CH₃—CH₂—CH₂— | CH≡C—CH₂— | (4-Br—Ph)—C≡C—CH₂— |
| 247 | (CH₃)₂CH— | CH≡C—CH₂— | (4-Br—Ph)—C≡C—CH₂— |
| 248 | Cl—CH₂—CH₂—CH₂— | CH≡C—CH₂— | (4-Br—Ph)—C≡C—CH₂— |
| 249 | CH₃— | CH₃—CH₂—CH(CH₃)— | (4-Br—Ph)—C≡C—CH₂— |
| 250 | CH₃—CH₂— | CH₃—CH₂—CH(CH₃)— | (4-Br—Ph)—C≡C—CH₂— |
| 251 | (CH₃)₂N— | CH₃—CH₂—CH(CH₃)— | (4-Br—Ph)—C≡C—CH₂— |
| 252 | CH₃—CH₂—CH₂— | CH₃—CH₂—CH(CH₃)— | (4-Br—Ph)—C≡C—CH₂— |
| 253 | (CH₃)₂CH— | CH₃—CH₂—CH(CH₃)— | (4-Br—Ph)—C≡C—CH₂— |
| 254 | Cl—CH₂—CH₂—CH₂— | CH₃—CH₂—CH(CH₃)— | (4-Br—Ph)—C≡C—CH₂— |
| 255 | CH₃— | CH₃—CH₂— | H |
| 256 | CH₃—CH₂— | CH₃—CH₂— | H |
| 257 | (CH₃)₂N— | CH₃—CH₂— | H |
| 258 | CH₃—CH₂—CH₂— | CH₃—CH₂— | H |
| 259 | (CH₃)₂CH— | CH₃—CH₂— | H |
| 260 | Cl—CH₂—CH₂—CH₂— | CH₃—CH₂— | H |
| 261 | CH₃— | (CH₃)₂CH— | H |
| 262 | CH₃—CH₂— | (CH₃)₂CH— | H |
| 263 | (CH₃)₂N— | (CH₃)₂CH— | H |
| 264 | CH₃—CH₂—CH₂— | (CH₃)₂CH— | H |
| 265 | (CH₃)₂CH— | (CH₃)₂CH— | H |
| 266 | Cl—CH₂—CH₂—CH₂— | (CH₃)₂CH— | H |
| 267 | CH₃— | CH₃—CH₂—CH₂— | H |
| 268 | CH₃—CH₂— | CH₃—CH₂—CH₂— | H |
| 269 | (CH₃)₂N— | CH₃—CH₂—CH₂— | H |
| 270 | CH₃—CH₂—CH₂— | CH₃—CH₂—CH₂— | H |
| 271 | (CH₃)₂CH— | CH₃—CH₂—CH₂— | H |
| 272 | Cl—CH₂—CH₂—CH₂— | CH₃—CH₂—CH₂— | H |

TABLE A-continued

| No. | R₁ | R₃ | R₈ |
|---|---|---|---|
| 273 | CH₃— | cyclopropyl-CH— | H |
| 274 | CH₃—CH₂— | cyclopropyl-CH— | H |
| 275 | (CH₃)₂N— | cyclopropyl-CH— | H |
| 276 | CH₃—CH₂—CH₂— | cyclopropyl-CH— | H |
| 277 | (CH₃)₂CH— | cyclopropyl-CH— | H |
| 278 | Cl—CH₂—CH₂—CH₂— | cyclopropyl-CH— | H |
| 279 | CH₃— | CH₂=CH—CH₂— | H |
| 280 | CH₃—CH₂— | CH₂=CH—CH₂— | H |
| 281 | (CH₃)₂N— | CH₂=CH—CH₂— | H |
| 282 | CH₃—CH₂—CH₂— | CH₂=CH—CH₂— | H |
| 283 | (CH₃)₂CH— | CH₂=CH—CH₂— | H |
| 284 | Cl—CH₂—CH₂—CH₂— | CH₂=CH—CH₂— | H |
| 285 | CH₃— | CH≡C—CH₂— | H |
| 286 | CH₃—CH₂— | CH≡C—CH₂— | H |
| 287 | (CH₃)₂N— | CH≡C—CH₂— | H |
| 288 | CH₃—CH₂—CH₂— | CH≡C—CH₂— | H |
| 289 | (CH₃)₂CH— | CH≡C—CH₂— | H |
| 290 | Cl—CH₂—CH₂—CH₂— | CH≡C—CH₂— | H |
| 291 | CH₃— | CH₃—CH₂—CH(CH₃)— | H |
| 292 | CH₃—CH₂— | CH₃—CH₂—CH(CH₃)— | H |
| 293 | (CH₃)₂N— | CH₃—CH₂—CH(CH₃)— | H |
| 294 | CH₃—CH₂—CH₂— | CH₃—CH₂—CH(CH₃)— | H |
| 295 | (CH₃)₂CH— | CH₃—CH₂—CH(CH₃)— | H |
| 296 | Cl—CH₂—CH₂—CH₂— | CH₃—CH₂—CH(CH₃)— | H |
| 297 | CH₃— | CH₃—CH₂— | Ph—CH₂— |
| 298 | CH₃—CH₂— | CH₃—CH₂— | Ph—CH₂— |
| 299 | (CH₃)₂N— | CH₃—CH₂— | Ph—CH₂— |
| 300 | CH₃—CH₂—CH₂— | CH₃—CH₂— | Ph—CH₂— |
| 301 | (CH₃)₂CH— | CH₃—CH₂— | Ph—CH₂— |
| 302 | Cl—CH₂—CH₂—CH₂— | CH₃—CH₂— | Ph—CH₂— |
| 303 | CH₃— | (CH₃)₂CH— | Ph—CH₂— |
| 304 | CH₃—CH₂— | (CH₃)₂CH— | Ph—CH₂— |
| 305 | (CH₃)₂N— | (CH₃)₂CH— | Ph—CH₂— |
| 306 | CH₃—CH₂—CH₂— | (CH₃)₂CH— | Ph—CH₂— |
| 307 | (CH₃)₂CH— | (CH₃)₂CH— | Ph—CH₂— |
| 308 | Cl—CH₂—CH₂—CH₂— | (CH₃)₂CH— | Ph—CH₂— |
| 309 | CH₃— | CH₃—CH₂—CH₂— | Ph—CH₂— |
| 310 | CH₃—CH₂— | CH₃—CH₂—CH₂— | Ph—CH₂— |
| 311 | (CH₃)₂N— | CH₃—CH₂—CH₂— | Ph—CH₂— |
| 312 | CH₃—CH₂—CH₂— | CH₃—CH₂—CH₂— | Ph—CH₂— |
| 313 | (CH₃)₂CH— | CH₃—CH₂—CH₂— | Ph—CH₂— |
| 314 | Cl—CH₂—CH₂—CH₂— | CH₃—CH₂—CH₂— | Ph—CH₂— |
| 315 | CH₃— | cyclopropyl-CH— | Ph—CH₂— |
| 316 | CH₃—CH₂— | cyclopropyl-CH— | Ph—CH₂— |
| 317 | (CH₃)₂N— | cyclopropyl-CH— | Ph—CH₂— |
| 318 | CH₃—CH₂—CH₂— | cyclopropyl-CH— | Ph—CH₂— |
| 319 | (CH₃)₂CH— | cyclopropyl-CH— | Ph—CH₂— |

TABLE A-continued

| No. | R₁ | R₃ | R₈ |
|---|---|---|---|
| 320 | Cl—CH₂—CH₂—CH₂— | CH— | Ph—CH₂— |
| 321 | CH₃— | CH₂=CH—CH₂— | Ph—CH₂— |
| 322 | CH₃—CH₂— | CH₂=CH—CH₂— | Ph—CH₂— |
| 323 | (CH₃)₂N— | CH₂=CH—CH₂— | Ph—CH₂— |
| 324 | CH₃—CH₂—CH₂— | CH₂=CH—CH₂— | Ph—CH₂— |
| 325 | (CH₃)₂CH— | CH₂=CH—CH₂— | Ph—CH₂— |
| 326 | Cl—CH₂—CH₂—CH₂— | CH₂=CH—CH₂— | Ph—CH₂— |
| 327 | CH₃— | CH≡C—CH₂— | Ph—CH₂— |
| 328 | CH₃—CH₂— | CH≡C—CH₂— | Ph—CH₂— |
| 329 | (CH₃)₂N— | CH≡C—CH₂— | Ph—CH₂— |
| 330 | CH₃—CH₂—CH₂— | CH≡C—CH₂— | Ph—CH₂— |
| 331 | (CH₃)₂CH— | CH≡C—CH₂— | Ph—CH₂— |
| 332 | Cl—CH₂—CH₂—CH₂— | CH≡C—CH₂— | Ph—CH₂— |
| 333 | CH₃— | CH₃—CH₂—CH(CH₃)— | Ph—CH₂— |
| 334 | CH₃—CH₂— | CH₃—CH₂—CH(CH₃)— | Ph—CH₂— |
| 335 | (CH₃)₂N— | CH₃—CH₂—CH(CH₃)— | Ph—CH₂— |
| 336 | CH₃—CH₂—CH₂— | CH₃—CH₂—CH(CH₃)— | Ph—CH₂— |
| 337 | (CH₃)₂CH— | CH₃—CH₂—CH(CH₃)— | Ph—CH₂— |
| 338 | Cl—CH₂—CH₂—CH₂— | CH₃—CH₂—CH(CH₃)— | Ph—CH₂— |
| 339 | CH₃— | CH₃—CH₂— | (4-Cl—Ph)—CH₂— |
| 340 | CH₃—CH₂— | CH₃—CH₂— | (4-Cl—Ph)—CH₂— |
| 341 | (CH₃)₂N— | CH₃—CH₂— | (4-Cl—Ph)—CH₂— |
| 342 | CH₃—CH₂—CH₂— | CH₃—CH₂— | (4-Cl—Ph)—CH₂— |
| 343 | (CH₃)₂CH— | CH₃—CH₂— | (4-Cl—Ph)—CH₂— |
| 344 | Cl—CH₂—CH₂—CH₂— | CH₃—CH₂— | (4-Cl—Ph)—CH₂— |
| 345 | CH₃— | (CH₃)₂CH— | (4-Cl—Ph)—CH₂— |
| 346 | CH₃—CH₂— | (CH₃)₂CH— | (4-Cl—Ph)—CH₂— |
| 347 | (CH₃)₂N— | (CH₃)₂CH— | (4-Cl—Ph)—CH₂— |
| 348 | CH₃—CH₂—CH₂— | (CH₃)₂CH— | (4-Cl—Ph)—CH₂— |
| 349 | (CH₃)₂CH— | (CH₃)₂CH— | (4-Cl—Ph)—CH₂— |
| 350 | Cl—CH₂—CH₂—CH₂— | (CH₃)₂CH— | (4-Cl—Ph)—CH₂— |
| 351 | CH₃— | CH₃—CH₂—CH₂— | (4-Cl—Ph)—CH₂— |
| 352 | CH₃—CH₂— | CH₃—CH₂—CH₂— | (4-Cl—Ph)—CH₂— |
| 353 | (CH₃)₂N— | CH₃—CH₂—CH₂— | (4-Cl—Ph)—CH₂— |
| 354 | CH₃—CH₂—CH₂— | CH₃—CH₂—CH₂— | (4-Cl—Ph)—CH₂— |
| 355 | (CH₃)₂CH— | CH₃—CH₂—CH₂— | (4-Cl—Ph)—CH₂— |
| 356 | Cl—CH₂—CH₂—CH₂— | CH₃—CH₂—CH₂— | (4-Cl—Ph)—CH₂— |
| 357 | CH₃— | CH— | (4-Cl—Ph)—CH₂— |
| 358 | CH₃—CH₂— | CH— | (4-Cl—Ph)—CH₂— |
| 359 | (CH₃)₂N— | CH— | (4-Cl—Ph)—CH₂— |
| 360 | CH₃—CH₂—CH₂— | CH— | (4-Cl—Ph)—CH₂— |
| 361 | (CH₃)₂CH— | CH— | (4-Cl—Ph)—CH₂— |
| 362 | Cl—CH₂—CH₂—CH₂— | CH— | (4-Cl—Ph)—CH₂— |
| 363 | CH₃— | CH₂=CH—CH₂— | (4-Cl—Ph)—CH₂— |
| 364 | CH₃—CH₂— | CH₂=CH—CH₂— | (4-Cl—Ph)—CH₂— |
| 365 | (CH₃)₂N— | CH₂=CH—CH₂— | (4-Cl—Ph)—CH₂— |
| 366 | CH₃—CH₂—CH₂— | CH₂=CH—CH₂— | (4-Cl—Ph)—CH₂— |
| 367 | (CH₃)₂CH— | CH₂=CH—CH₂— | (4-Cl—Ph)—CH₂— |
| 368 | Cl—CH₂—CH₂—CH₂— | CH₂=CH—CH₂— | (4-Cl—Ph)—CH₂— |
| 369 | CH₃— | CH≡C—CH₂— | (4-Cl—Ph)—CH₂— |
| 370 | CH₃—CH₂— | CH≡C—CH₂— | (4-Cl—Ph)—CH₂— |
| 371 | (CH₃)₂N— | CH≡C—CH₂— | (4-Cl—Ph)—CH₂— |
| 372 | CH₃—CH₂—CH₂— | CH≡C—CH₂— | (4-Cl—Ph)—CH₂— |
| 373 | (CH₃)₂CH— | CH≡C—CH₂— | (4-Cl—Ph)—CH₂— |
| 374 | Cl—CH₂—CH₂—CH₂— | CH≡C—CH₂— | (4-Cl—Ph)—CH₂— |
| 375 | CH₃— | CH₃—CH₂—CH(CH₃)— | (4-Cl—Ph)—CH₂— |
| 376 | CH₃—CH₂— | CH₃—CH₂—CH(CH₃)— | (4-Cl—Ph)—CH₂— |
| 378 | (CH₃)₂N— | CH₃—CH₂—CH(CH₃)— | (4-Cl—Ph)—CH₂— |

TABLE A-continued

| No. | $R_1$ | $R_3$ | $R_8$ |
|---|---|---|---|
| 379 | $CH_3-CH_2-CH_2-$ | $CH_3-CH_2-CH(CH_3)-$ | $(4\text{-}Cl-Ph)-CH_2-$ |
| 380 | $(CH_3)_2CH-$ | $CH_3-CH_2-CH(CH_3)-$ | $(4\text{-}Cl-Ph)-CH_2-$ |
| 381 | $Cl-CH_2-CH_2-CH_2-$ | $CH_3-CH_2-CH(CH_3)-$ | $(4\text{-}Cl-Ph)-CH_2-$ |
| 382 | $CH_3-$ | $CH_3-CH_2-$ | $(3\text{-}Cl-Ph)-CH_2-$ |
| 383 | $CH_3-CH_2-$ | $CH_3-CH_2-$ | $(3\text{-}Cl-Ph)-CH_2-$ |
| 384 | $(CH_3)_2N-$ | $CH_3-CH_2-$ | $(3\text{-}Cl-Ph)-CH_2-$ |
| 385 | $CH_3-CH_2-CH_2-$ | $CH_3-CH_2-$ | $(3\text{-}Cl-Ph)-CH_2-$ |
| 386 | $(CH_3)_2CH-$ | $CH_3-CH_2-$ | $(3\text{-}Cl-Ph)-CH_2-$ |
| 387 | $Cl-CH_2-CH_2-CH_2-$ | $CH_3-CH_2-$ | $(3\text{-}Cl-Ph)-CH_2-$ |
| 388 | $CH_3-$ | $(CH_3)_2CH-$ | $(3\text{-}Cl-Ph)-CH_2-$ |
| 389 | $CH_3-CH_2-$ | $(CH_3)_2CH-$ | $(3\text{-}Cl-Ph)-CH_2-$ |
| 390 | $(CH_3)_2N-$ | $(CH_3)_2CH-$ | $(3\text{-}Cl-Ph)-CH_2-$ |
| 391 | $CH_3-CH_2-CH_2-$ | $(CH_3)_2CH-$ | $(3\text{-}Cl-Ph)-CH_2-$ |
| 392 | $(CH_3)_2CH-$ | $(CH_3)_2CH-$ | $(3\text{-}Cl-Ph)-CH_2-$ |
| 393 | $Cl-CH_2-CH_2-CH_2-$ | $(CH_3)_2CH-$ | $(3\text{-}Cl-Ph)-CH_2-$ |
| 394 | $CH_3-$ | $CH_3-CH_2-CH_2-$ | $(3\text{-}Cl-Ph)-CH_2-$ |
| 395 | $CH_3-CH_2-$ | $CH_3-CH_2-CH_2-$ | $(3\text{-}Cl-Ph)-CH_2-$ |
| 396 | $(CH_3)_2N-$ | $CH_3-CH_2-CH_2-$ | $(3\text{-}Cl-Ph)-CH_2-$ |
| 397 | $CH_3-CH_2-CH_2-$ | $CH_3-CH_2-CH_2-$ | $(3\text{-}Cl-Ph)-CH_2-$ |
| 398 | $(CH_3)_2CH-$ | $CH_3-CH_2-CH_2-$ | $(3\text{-}Cl-Ph)-CH_2-$ |
| 399 | $Cl-CH_2-CH_2-CH_2-$ | $CH_3-CH_2-CH_2-$ | $(3\text{-}Cl-Ph)-CH_2-$ |
| 400 | $CH_3-$ | cyclopropyl-$CH-$ | $(3\text{-}Cl-Ph)-CH_2-$ |
| 401 | $CH_3-CH_2-$ | cyclopropyl-$CH-$ | $(3\text{-}Cl-Ph)-CH_2-$ |
| 402 | $(CH_3)_2N-$ | cyclopropyl-$CH-$ | $(3\text{-}Cl-Ph)-CH_2-$ |
| 403 | $CH_3-CH_2-CH_2-$ | cyclopropyl-$CH-$ | $(3\text{-}Cl-Ph)-CH_2-$ |
| 404 | $(CH_3)_2CH-$ | cyclopropyl-$CH-$ | $(3\text{-}Cl-Ph)-CH_2-$ |
| 405 | $Cl-CH_2-CH_2-CH_2-$ | cyclopropyl-$CH-$ | $(3\text{-}Cl-Ph)-CH_2-$ |
| 406 | $CH_3-$ | $CH_2=CH-CH_2-$ | $(3\text{-}Cl-Ph)-CH_2-$ |
| 407 | $CH_3-CH_2-$ | $CH_2=CH-CH_2-$ | $(3\text{-}Cl-Ph)-CH_2-$ |
| 408 | $(CH_3)_2N-$ | $CH_2=CH-CH_2-$ | $(3\text{-}Cl-Ph)-CH_2-$ |
| 409 | $CH_3-CH_2-CH_2-$ | $CH_2=CH-CH_2-$ | $(3\text{-}Cl-Ph)-CH_2-$ |
| 410 | $(CH_3)_2CH-$ | $CH_2=CH-CH_2-$ | $(3\text{-}Cl-Ph)-CH_2-$ |
| 411 | $Cl-CH_2-CH_2-CH_2-$ | $CH_2=CH-CH_2-$ | $(3\text{-}Cl-Ph)-CH_2-$ |
| 412 | $CH_3-$ | $CH\equiv C-CH_2-$ | $(3\text{-}Cl-Ph)-CH_2-$ |
| 413 | $CH_3-CH_2-$ | $CH\equiv C-CH_2-$ | $(3\text{-}Cl-Ph)-CH_2-$ |
| 414 | $(CH_3)_2N-$ | $CH\equiv C-CH_2-$ | $(3\text{-}Cl-Ph)-CH_2-$ |
| 415 | $CH_3-CH_2-CH_2-$ | $CH\equiv C-CH_2-$ | $(3\text{-}Cl-Ph)-CH_2-$ |
| 416 | $(CH_3)_2CH-$ | $CH\equiv C-CH_2-$ | $(3\text{-}Cl-Ph)-CH_2-$ |
| 417 | $Cl-CH_2-CH_2-CH_2-$ | $CH\equiv C-CH_2-$ | $(3\text{-}Cl-Ph)-CH_2-$ |
| 418 | $CH_3-$ | $CH_3-CH_2-CH(CH_3)-$ | $(3\text{-}Cl-Ph)-CH_2-$ |
| 419 | $CH_3-CH_2-$ | $CH_3-CH_2-CH(CH_3)-$ | $(3\text{-}Cl-Ph)-CH_2-$ |
| 420 | $(CH_3)_2N-$ | $CH_3-CH_2-CH(CH_3)-$ | $(3\text{-}Cl-Ph)-CH_2-$ |
| 421 | $CH_3-CH_2-CH_2-$ | $CH_3-CH_2-CH(CH_3)-$ | $CH(CH_3)-(3\text{-}Cl-Ph)-CH_2-$ |
| 422 | $(CH_3)_2CH-$ | $CH_3-CH_2-CH(CH_3)-$ | $(3\text{-}Cl-Ph)-CH_2-$ |
| 423 | $Cl-CH_2-CH_2-CH_2-$ | $CH_3-CH_2-CH(CH_3)-$ | $(3\text{-}Cl-Ph)-CH_2-$ |
| 424 | $CH_3-$ | $CH_3-CH_2-$ | $(3\text{-}CF_3-Ph)-CH_2-$ |
| 425 | $CH_3-CH_2-$ | $CH_3-CH_2-$ | $(3\text{-}CF_3-Ph)-CH_2-$ |
| 426 | $(CH_3)_2N-$ | $CH_3-CH_2-$ | $(3\text{-}CF_3-Ph)-CH_2-$ |
| 427 | $CH_3-CH_2-CH_2-$ | $CH_3-CH_2-$ | $(3\text{-}CF_3-Ph)-CH_2-$ |
| 428 | $(CH_3)_2CH-$ | $CH_3-CH_2-$ | $(3\text{-}CF_3-Ph)-CH_2-$ |
| 429 | $Cl-CH_2-CH_2-CH_2-$ | $CH_3-CH_2-$ | $(3\text{-}CF_3-Ph)-CH_2-$ |
| 430 | $CH_3-$ | $(CH_3)_2CH-$ | $(3\text{-}CF_3-Ph)-CH_2-$ |
| 431 | $CH_3-CH_2-$ | $(CH_3)_2CH-$ | $(3\text{-}CF_3-Ph)-CH_2-$ |
| 432 | $(CH_3)_2N-$ | $(CH_3)_2CH-$ | $(3\text{-}CF_3-Ph)-CH_2-$ |
| 433 | $CH_3-CH_2-CH_2-$ | $(CH_3)_2CH-$ | $(3\text{-}CF_3-Ph)-CH_2-$ |
| 434 | $(CH_3)_2CH-$ | $(CH_3)_2CH-$ | $(3\text{-}CF_3-Ph)-CH_2-$ |
| 435 | $Cl-CH_2-CH_2-CH_2-$ | $(CH_3)_2CH-$ | $(3\text{-}CF_3-Ph)\text{-}CH_2-$ |
| 436 | $CH_3-$ | $CH_3-CH_2-CH_2-$ | $(3\text{-}CF_3-Ph)-CH_2-$ |
| 437 | $CH_3-CH_2-$ | $CH_3-CH_2-CH_2-$ | $(3\text{-}CF_3-Ph)-CH_2-$ |
| 438 | $(CH_3)_2N-$ | $CH_3-CH_2-CH_2-$ | $(3\text{-}CF_3-Ph)-CH_2-$ |

TABLE A-continued

| No. | $R_1$ | $R_3$ | $R_8$ |
|---|---|---|---|
| 439 | $CH_3-CH_2-CH_2-$ | $CH_3-CH_2-CH_2-$ | $(3-CF_3-Ph)-CH_2-$ |
| 440 | $(CH_3)_2CH-$ | $CH_3-CH_2-CH_2-$ | $(3-CF_3-Ph)-CH_2-$ |
| 441 | $Cl-CH_2-CH_2-CH_2-$ | $CH_3-CH_2-CH_2-$ | $(3-CF_3-Ph)-CH_2-$ |
| 442 | $CH_3-$ | cyclopropyl-CH— | $(3-CF_3-Ph)-CH_2-$ |
| 443 | $CH_3-CH_2-$ | cyclopropyl-CH— | $(3-CF_3-Ph)-CH_2-$ |
| 444 | $(CH_3)_2N-$ | cyclopropyl-CH— | $(3-CF_3-Ph)-CH_2-$ |
| 445 | $CH_3-CH_2-CH_2-$ | cyclopropyl-CH— | $(3-CF_3-Ph)-CH_2-$ |
| 446 | $(CH_3)_2CH-$ | cyclopropyl-CH— | $(3-CF_3-Ph)-CH_2-$ |
| 447 | $Cl-CH_2-CH_2-CH_2-$ | cyclopropyl-CH— | $(3-CF_3-Ph)-CH_2-$ |
| 448 | $CH_3-$ | $CH_2=CH-CH_2-$ | $(3-CF_3-Ph)-CH_2-$ |
| 449 | $CH_3-CH_2-$ | $CH_2=CH-CH_2-$ | $(3-CF_3-Ph)-CH_2-$ |
| 450 | $(CH_3)_2N-$ | $CH_2=CH-CH_2-$ | $(3-CF_3-Ph)-CH_2-$ |
| 451 | $CH_3-CH_2-CH_2-$ | $CH_2=CH-CH_2-$ | $(3-CF_3-Ph)-CH_2-$ |
| 452 | $(CH_3)_2CH-$ | $CH_2=CH-CH_2-$ | $(3-CF_3-Ph)-CH_2-$ |
| 453 | $Cl-CH_2-CH_2-CH_2-$ | $CH_2=CH-CH_2-$ | $(3-CF_3-Ph)-CH_2-$ |
| 454 | $CH_3-$ | $CH\equiv C-CH_2-$ | $(3-CF_3-Ph)-CH_2-$ |
| 455 | $CH_3-CH_2-$ | $CH\equiv C-CH_2-$ | $(3-CF_3-Ph)-CH_2-$ |
| 456 | $(CH_3)_2N-$ | $CH\equiv C-CH_2-$ | $(3-CF_3-Ph)-CH_2-$ |
| 457 | $CH_3-CH_2-CH_2-$ | $CH\equiv C-CH_2-$ | $(3-CF_3-Ph)-CH_2-$ |
| 458 | $(CH_3)_2CH-$ | $CH\equiv C-CH_2-$ | $(3-CF_3-Ph)-CH_2-$ |
| 459 | $Cl-CH_2-CH_2-CH_2-$ | $CH\equiv C-CH_2-$ | $(3-CF_3-Ph)-CH_2-$ |
| 460 | $CH_3-$ | $CH_3-CH_2-CH(CH_3)-$ | $(3-CF_3-Ph)-CH_2-$ |
| 461 | $CH_3-CH_2-$ | $CH_3-CH_2-CH(CH_3)-$ | $(3-CF_3-Ph)-CH_2-$ |
| 462 | $(CH_3)_2N-$ | $CH_3-CH_2-CH(CH_3)-$ | $(3-CF_3-Ph)-CH_2-$ |
| 463 | $CH_3-CH_2-CH_2-$ | $CH_3-CH_2-CH(CH_3)-$ | $(3-CF_3-Ph)-CH_2-$ |
| 464 | $(CH_3)_2CH-$ | $CH_3-CH_2-CH(CH_3)-$ | $(3-CF_3-Ph)-CH_2-$ |
| 465 | $Cl-CH_2-CH_2-CH_2-$ | $CH_3-CH_2-CH(CH_3)-$ | $(3-CF_3-Ph)-CH_2-$ |

TABLE 7

Compounds represented by the Formula I.7 where the combination of the groups $R_1$, and $R_3$ corresponds to each row in table B.

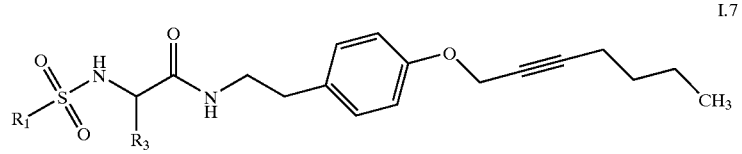

I.7

TABLE 8

Compounds represented by the Formula I.8 where the combination of the groups $R_1$, and $R_3$ corresponds to each row in table B.

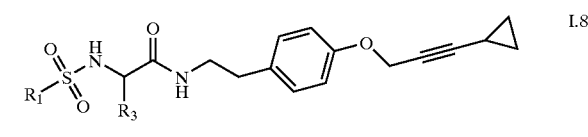

I.8

TABLE 9

Compounds represented by the Formula I.9 where the combination of the groups $R_1$, and $R_3$ corresponds to each row in table B.

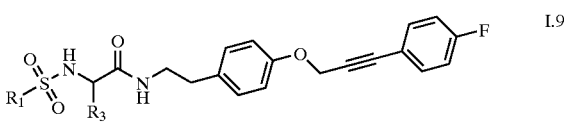

I.9

TABLE 10

Compounds represented by the Formula I.10 where the combination of the groups $R_1$, and $R_3$ corresponds to each row in table B.

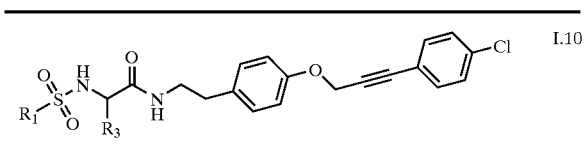

I.10

TABLE 11

Compounds represented by the Formula I.11 where the combination of the groups $R_1$, and $R_3$ corresponds to each row in table B.

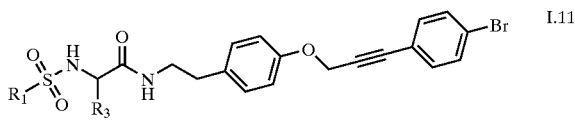

I.11

TABLE 12

Compounds represented by the Formula I.12 where the combination of the groups $R_1$, and $R_3$ corresponds to each row in table B.

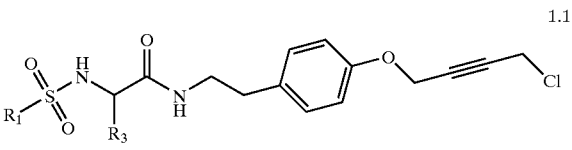

I.12

TABLE B

| No. | $R_1$ | $R_3$ |
|---|---|---|
| 001 | $(CH_3-CH_2)_2N-$ | $CH_3-CH_2-$ |
| 002 | $CH_3-CH_2-(CH_3)N-$ | $CH_3-CH_2-$ |
| 003 | pyrrolidin-1-yl | $CH_3-CH_2-$ |
| 004 | $CH_3-(CH_2)_2-CH_2-$ | $CH_3-CH_2-$ |
| 005 | $(CH_3)_2CH-CH_2-$ | $CH_3-CH_2-$ |
| 006 | $CH_3-CH_2-(CH_3)CH-$ | $CH_3-CH_2-$ |
| 007 | $(CH_3)_3C-$ | $CH_3-CH_2-$ |
| 008 | $CH_2=CH-$ | $CH_3-CH_2-$ |
| 009 | cyclohexyl-CH- | $CH_3-CH_2-$ |
| 010 | $(CH_3-CH_2)_2N-$ | $(CH_3)_2CH-$ |
| 011 | $CH_3-CH_2-(CH_3)N-$ | $(CH_3)_2CH-$ |
| 012 | pyrrolidin-1-yl | $(CH_3)_2CH-$ |
| 013 | $CH_3-(CH_2)_2-CH_2-$ | $(CH_3)_2CH-$ |
| 014 | $(CH_3)_2CH-CH_2-$ | $(CH_3)_2CH-$ |
| 015 | $CH_3-CH_2-(CH_3)CH-$ | $(CH_3)_2CH-$ |
| 016 | $(CH_3)_3C-$ | $(CH_3)_2CH-$ |
| 017 | $CH_2=CH-$ | $(CH_3)_2CH-$ |

TABLE B-continued

| No. | $R_1$ | $R_3$ |
|---|---|---|
| 018 | cyclohexyl-CH- | $(CH_3)_2CH-$ |
| 019 | $(CH_3-CH_2)_2N-$ | $CH_3-CH_2-CH_2$ |
| 020 | $CH_3-CH_2-(CH_3)N-$ | $CH_3-CH_2-CH_2$ |
| 021 | pyrrolidin-1-yl | $CH_3-CH_2-CH_2$ |
| 022 | $CH_3-(CH_2)_2-CH_2-$ | $CH_3-CH_2-CH_2$ |
| 023 | $(CH_3)_2CH-CH_2-$ | $CH_3-CH_2-CH_2$ |
| 024 | $CH_3-CH_2-(CH_3)CH-$ | $CH_3-CH_2-CH_2$ |
| 025 | $(CH_3)_3C-$ | $CH_3-CH_2-CH_2$ |
| 026 | $CH_2=CH-$ | $CH_3-CH_2-CH_2$ |
| 027 | cyclohexyl-CH- | $CH_3-CH_2-CH_2$ |
| 028 | $(CH_3-CH_2)_2N-$ | $CH_3-CH_2-(CH_3)CH-$ |
| 029 | $CH_3-CH_2-(CH_3)N-$ | $CH_3-CH_2-(CH_3)CH-$ |
| 030 | pyrrolidin-1-yl | $CH_3-CH_2-(CH_3)CH-$ |
| 031 | $CH_3-(CH_2)_2-CH_2-$ | $CH_3-CH_2-(CH_3)CH-$ |
| 032 | $(CH_3)_2CH-CH_2-$ | $CH_3-CH_2-(CH_3)CH-$ |
| 033 | $CH_3-CH_2-(CH_3)CH-$ | $CH_3-CH_2-(CH_3)CH-$ |
| 034 | $(CH_3)_3C-$ | $CH_3-CH_2-(CH_3)CH-$ |
| 035 | $CH_2=CH-$ | $CH_3-CH_2-(CH_3)CH-$ |
| 036 | cyclohexyl-CH- | $CH_3-CH_2-(CH_3)CH-$ |
| 037 | $(CH_3-CH_2)_2N-$ | cyclopropyl-CH- |
| 038 | $CH_3-CH_2-(CH_3)N-$ | cyclopropyl-CH- |
| 039 | pyrrolidin-1-yl | cyclopropyl-CH- |
| 040 | $CH_3(CH_2)_2-CH_2-$ | cyclopropyl-CH- |
| 041 | $(CH_3)_2CH-CH_2-$ | cyclopropyl-CH- |
| 042 | $CH_3-CH_2-(CH_3)CH-$ | cyclopropyl-CH- |
| 043 | $(CH_3)_3C-$ | cyclopropyl-CH- |
| 044 | $CH_2=CH-$ | cyclopropyl-CH- |
| 045 | cyclohexyl-CH- | cyclopropyl-CH- |
| 046 | $CH_3-$ | $HO-CH_2-$ |

TABLE B-continued

| No. | R₁ | R₃ |
|---|---|---|
| 047 | $CH_3-CH_2-$ | $HO-CH_2-$ |
| 048 | $(CH_3)_2N-$ | $HO-CH_2-$ |
| 049 | $CH_3-CH_2-CH_2-$ | $HO-CH_2-$ |
| 050 | $(CH_3)_2CH-$ | $HO-CH_2-$ |
| 051 | $CH_3-CH_2-(CH_3)CH-$ | $HO-CH_2-$ |
| 052 | $CH_3-$ | $HO-(CH_3)CH-$ |
| 053 | $CH_3-CH_2-$ | $HO-(CH_3)CH-$ |
| 054 | $(CH_3)_2N-$ | $HO-(CH_3)CH-$ |
| 055 | $CH_3-CH_2-CH_2-$ | $HO-(CH_3)CH-$ |
| 056 | $(CH_3)_2CH-$ | $HO-(CH_3)CH-$ |
| 057 | $CH_3-CH_2-(CH_3)CH-$ | $HO-(CH_3)CH-$ |
| 058 | $CH_3-$ | $(CH_3)_3C-O-(CH_3)CH-$ |
| 059 | $CH_3-CH_2-$ | $(CH_3)_3C-O-(CH_3)CH-$ |
| 060 | $(CH_3)_2N-$ | $(CH_3)_3C-O-(CH_3)CH-$ |
| 061 | $CH_3-CH_2-CH_2-$ | $(CH_3)_3C-O-(CH_3)CH-$ |
| 062 | $(CH_3)_2CH-$ | $(CH_3)_3C-O-(CH_3)CH-$ |
| 063 | $CH_3-CH_2-(CH_3)CH-$ | $(CH_3)_3C-O-(CH_3)CH-$ |
| 064 | $CH_3-$ | $CH_3-S-CH_2-CH_2-$ |
| 065 | $CH_3-CH_2-$ | $CH_3-S-CH_2-CH_2-$ |
| 066 | $(CH_3)_2N-$ | $CH_3-S-CH_2-CH_2-$ |
| 067 | $CH_3-CH_2-CH_2-$ | $CH_3-S-CH_2-CH_2-$ |
| 068 | $(CH_3)_2CH-$ | $CH_3-S-CH_2-CH_2-$ |
| 069 | $CH_3-CH_2-(CH_3)CH-$ | $CH_3-S-CH_2-CH_2-$ |
| 070 | $CH_3-$ | $HS-CH_2-CH_2-$ |
| 071 | $CH_3-CH_2-$ | $HS-CH_2-CH_2-$ |
| 072 | $(CH_3)_2N-$ | $HS-CH_2-CH_2-$ |
| 073 | $CH_3-CH_2-CH_2-$ | $HS-CH_2-CH_2-$ |
| 074 | $(CH_3)_2CH-$ | $HS-CH_2-CH_2-$ |
| 075 | $CH_3-CH_2-(CH_3)CH-$ | $HS-CH_2-CH_2-$ |
| 076 | $CH_3-$ | $(CH_3)_3C-$ |
| 077 | $CH_3-CH_2-$ | $(CH_3)_3C-$ |
| 078 | $(CH_3)_2N-$ | $(CH_3)_3C-$ |
| 079 | $CH_3-CH_2-CH_2-$ | $(CH_3)_3C-$ |
| 080 | $(CH_3)_2CH-$ | $(CH_3)_3C-$ |
| 081 | $CH_3-CH_2-(CH_3)CH-$ | $(CH_3)_3C-$ |

TABLE 13

Compounds represented by the Formula I.13 where the combination of the group $R_8$ corresponds to each row in table C.

I.13

TABLE 14

Compounds represented by the Formula I.14 where the combination of the group $R_8$ corresponds to each row in table C.

I.14

TABLE 15

Compounds represented by the Formula 1.15 where the combination of the group $R_8$ corresponds to each row in table C.

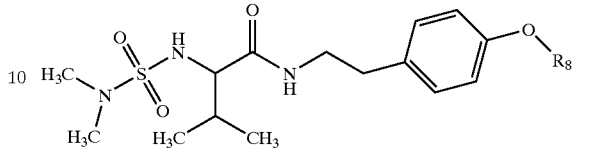

1.15

TABLE C

| No. | R₈ |
|---|---|
| 001 | $CH_3-CH_2-C(CH_3)H-C\equiv C-CH_2-$ |
| 002 | $(CH_3)_3C-C\equiv C-CH_2-$ |
| 003 | $(CH_3)_2CH-CH_2-C\equiv C-CH_2-$ |
| 004 | $CH_3-(CH_2)_4-C\equiv C-CH_2-$ |
| 005 | cyclopentyl$-C\equiv C-CH_2-$ |
| 006 | cyclohexyl$-C\equiv C-CH_2-$ |
| 007 | $(4-CH_3-Ph)-C\equiv C-CH_2-$ |
| 008 | $(2-Cl-Ph)-C\equiv C-CH_2-$ |
| 009 | $(3-Cl-Ph)-C\equiv C-CH_2-$ |
| 010 | $(3-Br-Ph)-C\equiv C-CH_2-$ |
| 011 | $(3-F-Ph)-C\equiv C-CH_2-$ |
| 012 | $(3-CH_3-Ph)-C\equiv C-CH_2-$ |
| 013 | $(2,4-di-Cl-Ph)-C\equiv C-CH_2-$ |
| 014 | $(3,4-di-Cl-Ph)-C\equiv C-CH_2-$ |
| 015 | $(3,4-di-F-Ph)-C\equiv C-CH_2-$ |
| 016 | $(3-CH_3-4-Cl-Ph)-C\equiv C-CH_2-$ |
| 017 | $(3-CH_3-4-Br-Ph)-C\equiv C-CH_2-$ |
| 018 | $(3-CF_3-Ph)-C\equiv C-CH_2-$ |
| 019 | $(4-CF_3O-Ph)-C\equiv C-CH_2-$ |
| 020 | $(4-Et-Ph)-C\equiv C-CH_2-$ |
| 021 | $[4-(CH_3)_3C-Ph]-C\equiv C-CH_2-$ |
| 022 | $(4-CH_2=CH-Ph)-C\equiv C-CH_2-$ |
| 023 | $(4-CH\equiv C-Ph)-C\equiv C-CH_2-$ |
| 024 | $(4-CH_3-CO-Ph)-C\equiv C-CH_2-$ |
| 025 | $(4-CH_3OOC-Ph)-C\equiv C-CH_2-$ |
| 026 | $(4-CH_3O-Ph)-C\equiv C-CH_2-$ |
| 027 | naphthyl$-C\equiv C-CH_2-$ |
| 028 | thienyl$-C\equiv C-CH_2-$ |
| 029 | pyridyl$-C\equiv C-CH_2-$ |
| 030 | pyrazinyl$-C\equiv C-CH_2-$ |
| 031 | $Ph-(CH_3)CH-$ |
| 032 | $Ph-(CH_3)_2C-$ |
| 033 | $(3-F-Ph)-CH_2-$ |

TABLE C-continued

| No. | $R_8$ |
|---|---|
| 034 | (4-Br—Ph)—CH$_2$— |
| 035 | (4-J—Ph)—CH$_2$— |
| 036 | (4-CH$_3$—Ph)—CH$_2$— |
| 037 | (4-CH$_3$O—Ph)—CH$_2$— |
| 038 | (4-CF$_3$O—Ph)—CH$_2$— |
| 039 | (4-F—Ph)—CH$_2$— |
| 040 | (2,4-di-F—Ph)—CH$_2$— |
| 041 | (3,4-di-F—Ph)—CH$_2$— |
| 042 | (3,4-di-Br—Ph)—CH$_2$— |
| 043 | (3,4-di-Cl—Ph)—CH$_2$— |
| 044 | (3-Cl-4-CH$_{3-Ph}$)—CH$_2$— |
| 045 | (3-CH$_3$-4-Cl—Ph)—CH$_2$— |
| 046 | (2,4,5-tri-Cl—Ph)—CH$_2$— |
| 047 | 1-naphthyl-CH$_2$— |
| 048 | 2-naphthyl-CH$_2$— |
| 049 | (thien-2-yl)-W |
| 050 | (5-Cl-thien-2-yl)-CH$_2$— |
| 051 | (5-Br-thien-2-yl)-CH$_2$— |
| 052 | (4,5-di-Br-thien-2-yl)-CH$_2$— |
| 053 | (pyridin-3-yl)-CH$_2$— |
| 054 | (6-Cl-pyridin-3-yl)-CH$_2$— |
| 055 | (3-Cl-5-CF$_3$-pyridin-2-yl)-CH$_2$— |
| 056 | (quinolin-2-yl)-CH$_2$— |
| 057 | Ph—CH=CH—CH$_2$— |
| 058 | (4-Cl—Ph)—CH=CH—CH$_2$— |
| 059 | (4-F—Ph)—CH=CH—CH$_2$— |
| 060 | (4-Br—Ph)—CH=CH—CH$_2$— |
| 061 | (3-CF$_3$—Ph)—CH=CH—CH$_2$— |
| 062 | Ph—CH$_2$—CH$_2$— |
| 063 | Ph—(CH$_2$)$_2$—CH$_2$— |
| 064 | (4-Cl—Ph)—(CH$_2$)$_2$—CH$_2$— |
| 065 | (4-Br—Ph)—(CH$_2$)$_2$—CH$_2$— |
| 066 | Ph—O—CH$_2$—CH$_2$— |
| 067 | (4-Cl—Ph)—O—CH$_2$—CH$_2$— |
| 068 | (4-F—Ph)—O—CH$_2$—CH$_2$— |
| 069 | (4-Br—Ph)—O—CH$_2$—CH$_2$— |
| 070 | (3-F—Ph)—O—CH$_2$—CH$_2$— |
| 071 | (3,4-di-Cl—Ph)—O—CH$_2$—CH$_2$— |
| 072 | (4-Cl—Ph)—O—(CH$_3$)CH—CH$_2$— |
| 073 | (3,4-di-Cl—Ph)—O—(CH$_3$)CH—CH$_2$— |
| 074 | Ph—N(CH$_3$)—CH$_2$—CH$_2$— |
| 075 | Ph—N(CH$_2$—CH$_3$)—CH$_2$—CH$_2$— |
| 076 | Ph—S—CH$_2$—CH$_2$— |
| 077 | (4-Cl—Ph)—S—CH$_2$—CH$_2$— |

Formulations may be prepared analogously to those described in, for example, WO 95/30651.

BIOLOGICAL EXAMPLES

D-1: Action Against Plasmopara viticola (Downy Mildew) on Vines 5 week old grape seedlings cv. Gutedel are treated with the formulated test compound in a spray chamber. One day after application grape plants are inoculated by spraying a sporangia suspension ($4 \times 10^4$ sporangia/ml) on the lower leaf side of the test plants. After an incubation period of 6 days at +21° C. and 95% r. h. in a greenhouse the disease incidence is assessed.

Compounds of Tables 1 to 15 exhibit a good fungicidal action against Plasmopara viticola on vines. Compounds A1.1, A1.2, A1.3, A1.4, A1.5 and A1.6 at 200 ppm inhibit fungal infestation in this test to a least 80%, while under the same conditions untreated control plants are infected by the phytopathogenic fungi to over 80%.

D-2: Action Against Phytophthora (Late Blight) on Tomato Plants 3 week old tomato plants cv. Roter Gnom are treated with the formulated test compound in a spray chamber. Two day after application the plants are inoculated by spraying a sporangia suspension ($2 \times 10^4$ sporangia/ml) on the test plants. After an incubation period of 4 days at +18° C. and 95% r. h. in a growth chamber the disease incidence is assessed. Compounds of Tables 1 to 15 exhibit a long-lasting effect against fungus infestation. Compounds A1.1, A1.2, A1.3, A1.4, A1.5 and A1.6 at 200 ppm inhibit fungal infestation in this test to a least 80%, while under the same conditions untreated control plants are infected by the phytopathogenic fungi to over 80%.

D-3: Action Against Phytophthora (Late Blight) on Potato Plants 5 week old potato plants cv. Bintje are treated with the formulated test compound in a spray chamber. Two day after application the plants are inoculated by spraying a sporangia suspension ($14 \times 10^4$ sporangia/ml) on the test plants. After an incubation period of 4 days at +18° C. and 95% r. h. in a growth chamber the disease incidence is assessed. Fungal infestation is effectively controlled with compounds of Tables 1 to 15. Compounds A1.1, A1.2, A1.3, A1.4, A1.5 and A1.6 at 200 ppm inhibit fungal infestation in this test to at least 80%, while under the same conditions untreated control plants are infected by the phytopathogenic fungi to over 80%.

What is claimed is:

1. α-sulfin- and α-sulfonamino acid amides of formula I

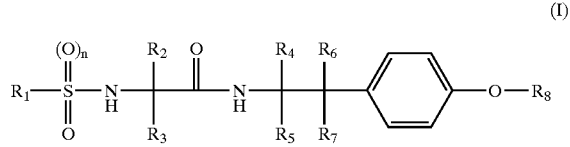

(I)

including the optical isomers thereof and mixtures of such isomers,
wherein n is a number zero or one;

$R_1$ is $C_1-C_{12}$alkyl, $C_1-C_{12}$alkyl substituted with $C_1-C_4$alkoxy, $C_1-C_4$alkylthio, $C_1-C_4$alkylsulfonyl, $C_3-C_8$cycloalkyl, cyano, $C_1-C_6$alkoxycarbonyl, $C_3-C_6$alkenyloxycarbonyl or $C_3-C_8$alkynyloxycarbonyl; $C_3-C_8$cycloalkyl; $C_2-C_{12}$alkenyl; $C_2-C_{12}$alkynyl; $C_1-C_{12}$halogenalkyl; or a group $NR_9R_{10}$ wherein $R_9$ and $R_{10}$ are each independently of the other $C_1-C_6$alkyl, or together are tetra- or penta-methylene;

$R_2$ and $R_3$ are each independently hydrogen; $C_1-C_8$alkyl; $C_1-C_8$alkyl substituted with hydroxy, mercapto, $C_1-C_4$alkoxy or $C_1-C_4$alkylthio; $C_3-C_8$alkenyl; $C_3-C_8$alkynyl; $C_3-C_8$cycloalkyl; $C_3-C_3$cycloalkyl-$C_1-C_4$alkyl; or the two groups $R_2$ and $R_3$ together with the carbon atom to which they are bonded form a three- to eight-membered hydrocarbon ring;

$R_4$, $R_5$, $R_6$ and $R_7$ are each independently hydrogen or $C_1-C_4$alkyl;

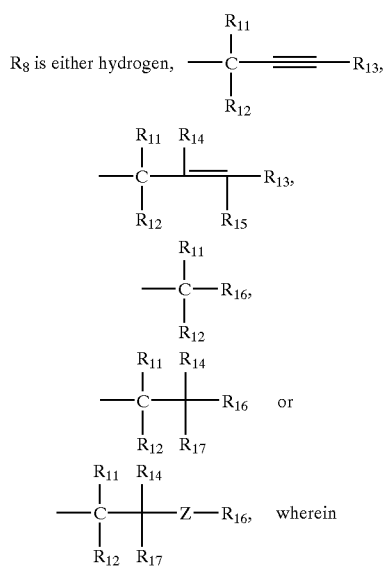

$R_{11}$, $R_{12}$, $R_{14}$, $R_{15}$ and $R_{17}$ are each independently hydrogen or $C_1-C_4$alkyl, $R_{13}$ is $C_4-C_{12}$alkyl; $C_1-C_{12}$halogenalkyl; $C_3-C_8$cycloalkyl; optionally substituted aryl or optionally substituted heteroaryl, $R_{16}$ is optionally substituted aryl or optionally substituted heteroaryl; and Z is oxygen, sulfur —$CR_{18}R_{19}$— or —$NR_{20}$—, wherein $R_{18}$, $R_{19}$ and $R_{20}$ independently of each other are hydrogen or $C_1-C_4$alkyl.

2. A compound according to claim 1 wherein n is one.

3. A compound of formula I according to claim 1 wherein $R_1$ is $C_1-C_{12}$alkyl, $C_1-C_{12}$alkyl substituted with $C_1-C_4$alkoxy, $C_1-C_4$alkylthio, or $C_1-C_4$alkylsulfonyl; $C_3-C_8$cycloalkyl; $C_2-C_{12}$alkenyl; $C_2-C_{12}$alkynyl; $C_1-C_{12}$halogenalkyl; or a group $NR_9R_{10}$ wherein $R_9$ and $R_{10}$ are each independently of the other hydrogen or $C_1-C_6$alkyl, or together are tetra- or penta-methylene.

4. A compound of formula I according to claim 1 wherein $R_2$ is hydrogen and $R_3$ is $C_1-C_8$alkyl, $C_1-C_8$alkyl, optionally substituted by hydroxy, $C_1-C_4$alkoxy, mercapto or $C_1-C_4$alkylthio; $C_3-C_8$alkenyl; $C_3-C_8$alkynyl; $C_3-C_8$cycloalkyl or $C_3-C_8$cycloalkyl-$C_1-C_4$alkyl.

5. A compound of formula I according to claim 1 wherein $R_4$ is hydrogen, methyl or ethyl.

6. A compound of formula I according to claim 1 wherein $R_5$, $R_6$ and $R_7$ are each independently hydrogen or methyl.

7. A compound of formula I according to claim 1 wherein $R_{11}$, $R_{12}$, $R_{14}$, $R_{15}$ and $R_{17}$ are each independently hydrogen or methyl.

8. A compound of formula I according to claim 1 wherein $R_{13}$ is $C_4-C_{12}$alkyl; $C_1-C_{12}$halogenalkyl; $C_3-C_8$cycloalkyl; optionally substituted aryl or optionally substituted heteroaryl consisting of one or two condensed five or six membered rings with 1 to 4 identical or different heteroatoms selected from oxygen, nitrogen or sulfur.

9. A compound of formula I according to claim 1 wherein $R_{16}$ is optionally substituted aryl or optionally substituted heteroaryl consisting of one or two condensed five or six membered rings with 1 to 4 identical or different heteroatoms selected from oxygen, nitrogen or sulfur.

10. A compound of formula I according to claim 1 wherein Z is oxygen, sulfur or —$CH_2$—.

11. A compound of formula I according to claim 1 wherein n is one;

$R_1$ is $C_1-C_4$alkyl, vinyl; $C_1-C_4$halogenalkyl; or dimethylamino;

$R_2$ is hydrogen and $R_3$ is isopropyl;

$R_4$, $R_5$, $R_6$, $R_7$, $R_{11}$, $R_{12}$, $R_{14}$, $R_{15}$ and $R_{17}$ are each hydrogen;

$R_{13}$ is $C_4-C_8$alkyl; $C_1-C_6$halogenalkyl; $C_3-C_8$cycloalkyl; phenyl, pyridyl, with each of the aromatic ring being optionally substituted by 1 to 3 substituents selected from the group consisting of $C_1-C_8$alkyl, $C_1-C_8$halogenalkyl, $C_1-C_8$alkoxy, $C_1-C_8$halogenalkoxy, $C_1-C_8$alkylthio, $C_1-C_8$halogenalkylthio, halogen, cyano, nitro and $C_1-C_8$alkoxycarbonyl;

$R_{16}$ is phenyl, pyridyl, with each of the aromatic ring being optionally substituted by 1 to 3 substituents selected from the group consisting of $C_1-C_8$alkyl, $C_1-C_8$halogenalky, $C_1-C_8$alkoxy, $C_1-C_8$halogenalkoxy, $C_1-C_8$alkylthio, $C_1-C_8$halogenalkylthio, halogen, cyano, nitro and $C_1-C_8$alkoxycarbonyl; and Z is oxygen.

12. A process for the preparation of a compound of formula I according to claim 1, which comprises reacting a) an amino acid of formula II or a carboxy-activated derivative thereof

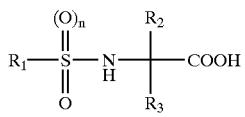 (II)

wherein $R_1$, n, $R_2$ and $R_3$ are as defined for formula I is reacted with an amine of formula III

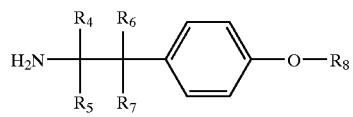 (III)

wherein $R_4$, $R_5$, $R_6$, $R_7$ and $R_8$ are as defined for formula I optionally in the presence of a base and optionally in the presence of a diluting agent, or b) an amino acid derivative of formula VI

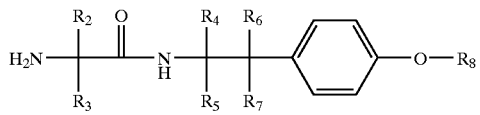 (VI)

wherein $R_2$, $R_3$, $R_4$, $R_5$, $R_6$, $R_7$ and $R_8$ are as defined for formula I with a sulfonyl halide or a sulfinyl halide of formula V

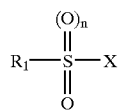 (V)

wherein $R_1$ and n are as defined for formula I and X is halide, preferentially chlorine or bromine, or c) a phenol of formula VII

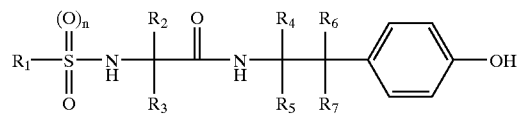 (VII)

wherein $R_1$, n, $R_2$, $R_3$, $R_4$, $R_5$, $R_6$ and $R_7$ are as defined for formula I with a compound of formula VIII $$Y-R_8 \quad (VIII)$$

wherein $R_8$ is as defined for formula I and Y is a leaving group like a halide such as a chloride or bromide or a sulfonic ester such as a tosylate, mesylate or triflate.

13. A process for the preparation of a compound of formula Ia

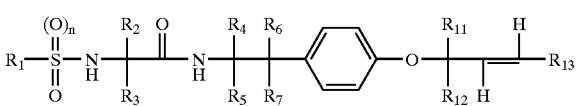 (Ia)

wherein $R_1$, n, $R_2$, $R_3$, $R_4$, $R_5$, $R_6$, $R_7$, $R_{11}$, $R_{12}$ and $R_{13}$ are defined in claim 1 for formula I which comprises reacting a compound of formula IX

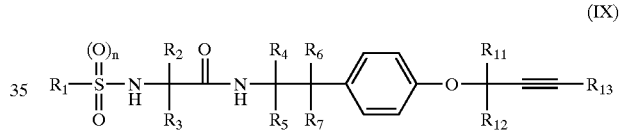 (IX)

wherein $R_1$, n, $R_2$, $R_3$, $R_4$, $R_5$, $R_6$, $R_7$, $R_{11}$, $R_{12}$ and $R_{13}$ are defined for formula I with hydrogen.

14. A composition for controlling and protecting against phytopathogenic microorganisms, comprising a compound of formula I according to claim 1 as active ingredient together with a suitable carrier.

15. A method of controlling and preventing an infestation of crop plants by phytopathogenic microorganisms, preferably fungal organisms, which comprises the application of a compound of formula I according to claim 1 as active ingredient to the plant, to parts of plants or to the locus thereof.

* * * * *